US012257442B2

(12) United States Patent
McDonald et al.

(10) Patent No.: US 12,257,442 B2
(45) Date of Patent: Mar. 25, 2025

(54) COMPUTER-ASSISTED PAIN MAPPING AND NEUROMODULATION SYSTEM

(71) Applicant: Boston Scientific Neuromodulation Corporation, Valencia, CA (US)

(72) Inventors: Matthew Lee McDonald, Glendale, CA (US); Benjamin Phillip Hahn, Austin, TX (US); Kyle Harish Srivastava, Saint Paul, MN (US); Amarpreet Singh Bains, Woodbury, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 306 days.

(21) Appl. No.: 17/518,282

(22) Filed: Nov. 3, 2021

(65) Prior Publication Data

US 2022/0134119 A1 May 5, 2022

Related U.S. Application Data

(60) Provisional application No. 63/109,453, filed on Nov. 4, 2020.

(51) Int. Cl.
*A61N 1/372* (2006.01)
*A61N 1/36* (2006.01)

(52) U.S. Cl.
CPC ..... *A61N 1/37247* (2013.01); *A61N 1/36071* (2013.01); *A61N 1/36132* (2013.01)

(58) Field of Classification Search
CPC ............ A61N 1/37247; A61N 1/36071; A61N 1/36132
See application file for complete search history.

(56) References Cited

U.S. PATENT DOCUMENTS

2008/0140163 A1 6/2008 Keacher et al.
2010/0305660 A1 12/2010 Hegi et al.
(Continued)

FOREIGN PATENT DOCUMENTS

WO WO-2022098763 A1 5/2022

OTHER PUBLICATIONS

"International Application Serial No. PCT/US2021/057903, International Preliminary Report on Patentability mailed May 19, 2023", 7 pgs.

(Continued)

*Primary Examiner* — Joseph M Dietrich
(74) *Attorney, Agent, or Firm* — Schwegman Lundberg & Woessner, P.A.

(57) ABSTRACT

This document discusses systems, devices, and methods for computer-assisted pain or paresthesia assessment and pain management in a subject. A system includes a programming aid device including a user interface, a transceiver circuit to receive information about pain management for the patient from one or more of a software-based virtual agent (SVA) or a human assistant other than the patient, and a controller circuit to initiate and manage information exchange session between the patient and one or more of the SVA or the human assistant, via the user interface, regarding pain or paresthesia sensation and pain management. Based on the information exchange, the controller determines a stimulation setting, and generate a therapy control signal to the neuromodulation device to initiate delivery of neuromodulation energy according to the determined stimulation setting.

20 Claims, 10 Drawing Sheets

(56) References Cited

U.S. PATENT DOCUMENTS

2011/0270358 A1* 11/2011 Davis .................... G06F 3/016
                                                     715/846
2012/0165619 A1   6/2012 Masoud et al.
2015/0127062 A1   5/2015 Holley
2017/0203111 A1   7/2017 Pless et al.
2019/0358457 A1* 11/2019 Kozloski ............ A61N 1/37235

OTHER PUBLICATIONS

"International Application Serial No. PCT/US2021/057903, International Search Report mailed Mar. 10, 2022", 4 pgs.
"International Application Serial No. PCT/US2021/057903, Written Opinion mailed Mar. 10, 2022", 5 pgs.
"Australian Application Serial No. 2021374656, First Examination Report mailed Apr. 15, 2024", 3 pgs.
"European Application Serial No. 21816589.2, Response to Communication Pursuant to Rules 161 & 162 filed Nov. 30, 2023", 11 pgs.

* cited by examiner

COMPUTER-ASSISTED PAIN MAPPING AND NEUROMODULATION SYSTEM

CLAIM OF PRIORITY

This application claims the benefit of U.S. Provisional Application No. 63/109,453, filed on Nov. 4, 2020, which is incorporated by reference herein in its entirety.

TECHNICAL FIELD

This document relates generally to medical systems and more particularly to systems, devices, and methods for pain management.

BACKGROUND

Pain is one of the most common and among the most personally compelling reasons for seeking medical attention, and consumes considerable healthcare resources each year. The relation between etiology, underlying mechanisms and the specific symptoms and signs related to painful disorders is complex. Pain in an individual patient may be produced by more than one mechanism.

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain. Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system).

Chronic pain may be treated or alleviated using medications, acupuncture, surgery, and neuromodulation therapy such as local electrical stimulation or brain stimulation, among others. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), which can electrically stimulate tissue or nerve centers to treat nervous or muscular disorders. In an example, an IPG can deliver electrical pulses to a specific region in a patient's spinal cord, such as particular spinal nerve roots or nerve bundles, to create an analgesic effect that masks pain sensation.

SUMMARY

This document discusses systems, devices, and methods for computer-assisted pain or paresthesia assessment, and programming of a neuromodulation device for pain management in a subject. An exemplary system includes a programming aid device including a user interface, a transceiver circuit to receive information about pain management for the patient from one or more of a software-based virtual agent (SVA) or a human assistant other than the patient, and a controller circuit to initiate and manage information exchange session between the patient and one or more of the SVA or the human assistant, via the user interface, regarding pain or paresthesia sensation and pain management. Based on the information exchange, the controller determines a stimulation setting, and generate a therapy control signal to the neuromodulation device to initiate delivery of neuromodulation energy according to the determined stimulation setting.

Example 1 is a system for computer-assisted programming of a neuromodulation device for pain management in a patient. The system comprises a programming aid device operable by the patient that comprises a user interface, a transceiver circuit configured to receive, from one or more of a software-based virtual agent (SVA) or a human assistant other than the patient, information about pain management for the patient; and a controller circuit. The controller circuit can be configured to: initiate and manage an information exchange session between the patient and one or more of the SVA or the human assistant, via the user interface, regarding pain or paresthesia perception and pain management of the patient; based on the information exchange, determine a stimulation setting for the neuromodulation device; and generate a therapy control signal to the neuromodulation device to initiate delivery of neuromodulation energy to the patient in accordance with the determined stimulation setting.

In Example 2, the subject matter of Example 1 optionally includes the programming aid device that can be a personal mobile electronic device.

In Example 3, the subject matter of any one or more of Examples 1-2 optionally includes the transceiver circuit that can be configured to communicate with at least one of a remote computing device hosting services including the SVA, or a user assistive device operable by the human assistant to provide the information about pain management.

In Example 4, the subject matter of Example 3 optionally includes the transceiver circuit that can be configured to communicate with the remote computing device including a cloud-computing device or networked devices.

In Example 5, the subject matter of any one or more of Examples 1-4 optionally includes the user interface that can be configured to present the exchanged information in one or more of textual, graphical, audio, or video forms.

In Example 6, the subject matter of any one or more of Examples 1-5 optionally includes the information exchange session that can include messages about pain or paresthesia perception of the patient including identifying one or more pain or paresthesia sites, and wherein the controller circuit is configured to generate a pain or paresthesia map based on the identified one or more pain or paresthesia sites.

In Example 7, the subject matter of Example 6 optionally includes the pain or paresthesia perception that can include determining one or more pain or paresthesia characteristics including an intensity, a type, or a quality of pain or paresthesia at respective one or more pain or paresthesia sites, and wherein the controller circuit is configured to generate a pain or paresthesia map further using at least one of the one or more pain or paresthesia characteristics.

In Example 8, the subject matter of any one or more of Examples 1-7 optionally includes the information exchange session that can include messages about identifying one or more stimulation sites to apply the neuromodulation energy or modified neuromodulation energy, and wherein the controller circuit is configured to determine the stimulation setting based on the identified one or more stimulation sites.

In Example 9, the subject matter of any one or more of Examples 1-8 optionally includes the information exchange session that can include messages about performing integrity testing or trouble-shooting of the neuromodulation device, and wherein the controller circuit is configured to initiate integrity testing or trouble-shooting of the neuromodulation device based on the exchanged messages.

In Example 10, the subject matter of any one or more of Examples 1-9 optionally includes the information exchange session that can include the SVA or the human assistant suggesting a stimulation setting for the neuromodulation device, and wherein the controller circuit is configured to determine the stimulation setting based on suggested stimulation setting.

In Example 11, the subject matter of any one or more of Examples 1-10 optionally includes the information exchange session that can include the human assistant confirming, overriding, or modifying a stimulation setting for the neuromodulation device suggested by the SVA or the patient, and wherein the controller circuit is configured to determine the stimulation setting based on the confirmation, override, or modification of the stimulation setting.

In Example 12, the subject matter of any one or more of Examples 1-11 optionally includes the controller circuit that can be configured to generate an alert to invite the human assistant to join the information exchange session responsive to a request by the patient or the SVA.

In Example 13, the subject matter of any one or more of Examples 1-12 optionally includes the controller circuit that can be configured to generate an alert to invite the human assistant to join the information exchange session responsive to a trigger event including at least one of: an identification of a new pain or paresthesia site; a new stimulation setting suggested by the SVA; a frequent reprogramming of therapy exceeding a threshold; or an outlier event during programming of therapy.

In Example 14, the subject matter of any one or more of Examples 1-13 optionally includes the controller circuit that can be configured to generate a control signal that permits or prohibits respective actions of one or more of the patient, the SVA, or the human assistant during the information exchange session.

In Example 15, the subject matter of any one or more of Examples 1-14 optionally includes the neuromodulation device that can be configured to, in response to the therapy control signal, deliver spinal cord stimulation in accordance with the determined stimulation setting.

Example 16 is a non-transitory machine-readable storage medium that includes instructions that, when executed by one or more processors of a machine, cause the machine to perform operations comprising: establishing communications between a programming aid device operable by a patient and one or more of (1) a remote computing device hosting a software-based virtual agent (SVA) or (2) a user assistive device operable by a human assistant other than the patient; initiating and managing an information exchange session, via the programming aid device, between the patient and one or more of the SVA or the human assistant regarding pain or paresthesia perception and pain management of the patient; presenting the information exchange session on a user interface of the programming aid device; based on the information exchange, determining a stimulation setting for a neuromodulation device; and generating a therapy control signal to the neuromodulation device to initiate delivery of neuromodulation energy to the patient in accordance with the determined stimulation setting.

In Example 17, the subject matter of Example 16 optionally includes the information exchange session includes messages presented in one or more of textual, graphical, audio, or video forms.

In Example 18, the subject matter of any one or more of Examples 16-17 optionally includes the information exchange session that can include messages about pain or paresthesia perception of the patient including identifying one or more pain or paresthesia sites, and wherein the instructions cause the machine to perform operations comprising generating a pain or paresthesia map based on the messages of pain or paresthesia perception.

In Example 19, the subject matter of any one or more of Examples 16-18 optionally includes the information exchange session that can include messages about identifying one or more stimulation sites to apply the neuromodulation energy or modified neuromodulation energy, and wherein the instructions cause the machine to perform operations comprising determining the stimulation setting based on the identified one or more stimulation sites.

In Example 20, the subject matter of any one or more of Examples 16-19 optionally includes the instructions causing the machine to perform operations that can include generating an alert to invite the human assistant to join the information exchange session responsive to a request by the patient or the SVA or a trigger event.

Example 21 is a method of programming of a neuromodulation device for pain management in a patient using a programming aid device. The method comprises: establishing communications between the programming aid device and one or more of (1) a remote computing device hosting a software-based virtual agent (SVA) or (2) a user assistive device operable by a human assistant other than the patient; initiating and managing an information exchange session, via the programming aid device, between the patient and one or more of the SVA or the human assistant regarding pain or paresthesia perception and pain management of the patient; presenting the information exchange session on a user interface of the programming aid device; based on the information exchange, determining a stimulation setting for the neuromodulation device; and generating a therapy control signal to the neuromodulation device to initiate delivery of neuromodulation energy to the patient in accordance with the determined stimulation setting.

In Example 22, the subject matter of Example 21 optionally includes the information exchange session that can include messages about pain or paresthesia perception of the patient including identifying one or more pain or paresthesia sites, and the method comprises generating a pain or paresthesia map based on the messages of pain or paresthesia perception.

In Example 23, the subject matter of any one or more of Examples 21-22 optionally includes the information exchange session that can include messages about identifying one or more stimulation sites to apply the neuromodulation energy or modified neuromodulation energy, and the method comprises determining the stimulation setting based on the identified one or more stimulation sites.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
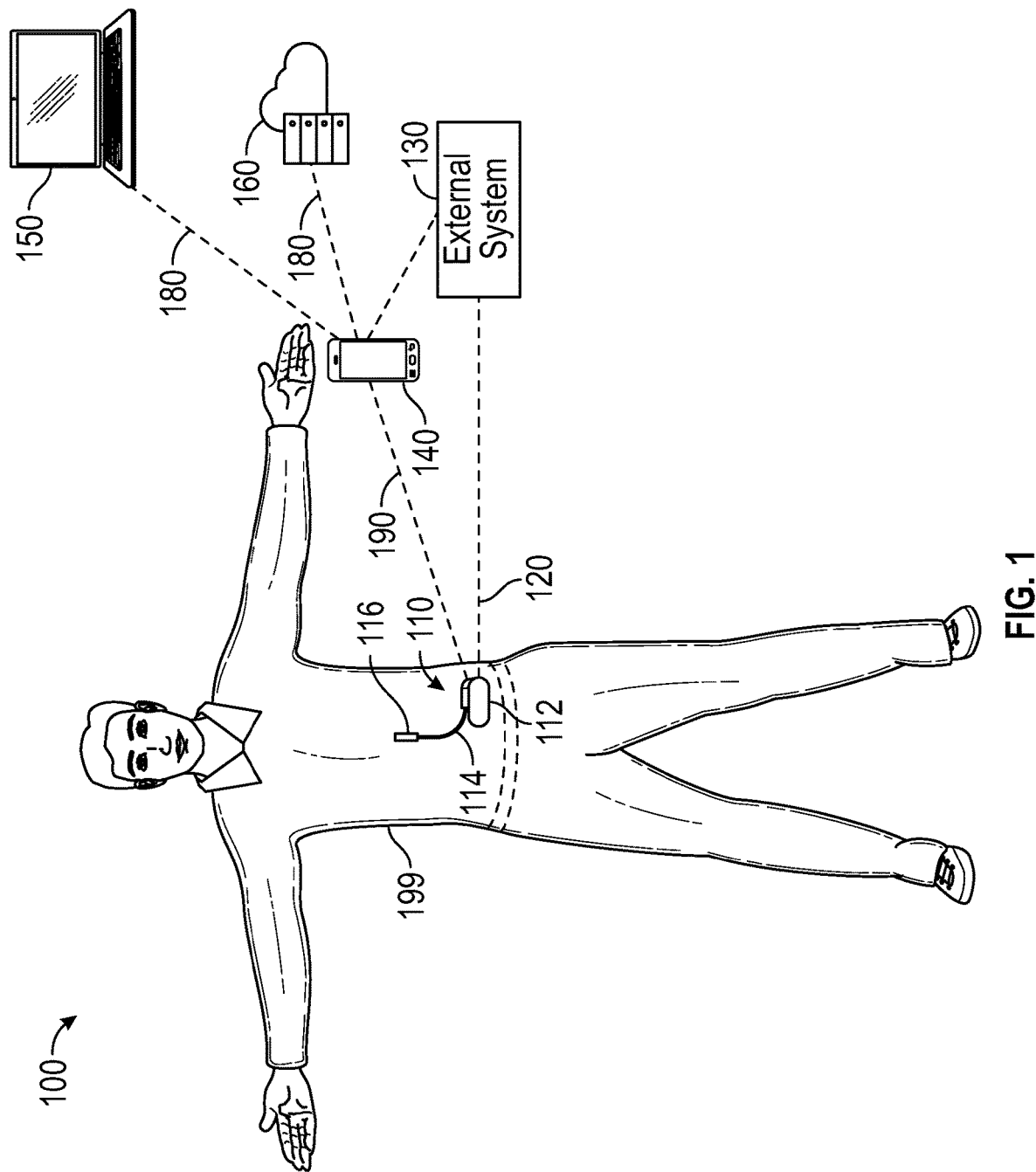
FIG. 1 illustrates, by way of example and not limitation, an example of a neuromodulation system and portions of an environment in which the neuromodulation system may operate.

By way of example, chronic pain management may involve determining appropriate treatment regimens such as SCS and evaluating therapy efficacy. Accurate pain assessment and characterization are desirable for managing patients with chronic pain. Currently, pain assessment generally relies on patient subjective report of pain or paresthesia symptoms, including severity, pattern, or duration of pain. Based on the patient report, a clinician may prescribe a pain therapy, such as to manually program an electrostimulator, or adjust a stimulation setting, to deliver a neuromodulation therapy in a clinical setting. This may have several disadvantages. First, the report or description of pain or paresthesia perception may be constrained by the patient cognitive abilities or knowledge about pain. Without additional help such as from a clinician, a caregiver, or a representative of an implantable pain management device manufacturer, some patients may find it difficult to identify exact body locations, or to qualify the nature, of their pain or paresthesia perception. Patients may use a diverse body of descriptors to describe their pain or paresthesia perception. The subjective pain description may also be subject to intra-patient variation such as due to a progression of a chronic disease, or a change in general health status or medication. Second, for patients in an ambulatory, non-clinical setting, programming of pain therapy by a clinician or a device expert (e.g., device manufacturer representative) may not be feasible especially if immediate therapy titration is required. For some patients and on some occasions, a remote, virtual visit with a clinician or a device expert may be more desirable and practical than a conventional in-person visit at a clinic. The present inventors have recognized that such a remotely-accessible pain management platform can be implanted to allow a patient to assess their pain or paresthesia perceptions, and configure their neuromodulation devices such as adjusting an electrostimulation setting for pain therapy with minimal or no direct intervention from others. Such a remotely-accessible pain management system may be empowered by advanced computing and networking technologies to provide improved pain management functionality and user experience.

Disclosed herein are systems, devices, and methods for computer-assisted pain or paresthesia assessment and pain management. According to various examples discussed herein, a programming aid device, operable by the patient, can be in communication with a pain modulation device, such as an implantable SCS device. The programming aid device may include a user interface, a transceiver circuit that receives information about pain management for the patient from one or more of a software-based virtual agent (SVA) or a human assistant other than the patient, and a controller circuit that may initiate and manage a session of information exchange between the patient and one or more of the SVA or the human assistant, via the user interface, regarding patient pain sensation and pain management. Based on the information exchange, the controller determines a stimulation setting, and generate a therapy control signal to the neuromodulation device to initiate delivery of neuromodulation energy according to the determined stimulation setting.

Pain management assisted by an SVA, as described in this document, may improve the technology of device-based pain assessment and management. According to one aspect of the present subject matter, a remotely-accessible pain management platform can be implemented in and executed by a personal mobile electronic device. The pain management platform interconnects the patient, the SVA, and/or one or more human assistants (e.g., a clinician, a caregiver, or a device expert such as a device manufacturer representative), and enables multi-party information exchange regarding patient pain or paresthesia perception, individualized pain therapy, or device integrity testing or trouble-shooting, among other capabilities. The pain management platform as described herein helps overcome geographic barriers to medical facilities and resources, which can be particularly beneficial for patients in medically underserved communities or geographic locations. Moreover, such a pain management platform may incorporate advanced computing and networking technologies to provide improved pain management functionality and user experience. According to one example, the SVA can be a cloud-based interactive chatbot providing artificial intelligence (AI)-based services and guidance on pain management for the patient. With the assistance from the SVA and from other networked parties (e.g., human assistants), a patient may use the present pain management platform to perform pain or paresthesia assessment, pain therapy adjustment and evaluation, or neuromodulation device check, among other tasks, with minimal or no direct in-person interventions with other professionals. The pain management platform may respond to patient inquires more quickly and more consistently, thereby increasing the efficiency of pain management and care delivery and improving user experience. With convenient user control, automated SVA assistance, and remote access by one or more human assistants, safety, reliability, and efficacy of individualized pain management can be maintained or improved. Timely delivery of individualized pain therapies may improve patient outcome, enhance battery longevity of an implantable neuromodulation device, and reduce clinic visits or hospitalization. Additionally, by accessing the pain management platform to remotely monitor the patient and supervise the SVA as needed, the human professionals may reduce their time for in-person interaction with patients yet without impairing the quality of patient care, and focus on more complex tasks that require more skills and critical thinking. Accordingly, the overall healthcare cost may be reduced.

The present system may be implemented using a combination of hardware and software designed to provide a pain management regimen to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, and Vagus Nerve Stimulation (VNS) therapies. In various examples, instead of providing closed-loop pain therapies, the systems, devices, and methods described herein may be used to monitor the patient and assess pain that either occurs intrinsically or is induced by nerve block procedures or radiofrequency ablation therapies, among others. The patient monitoring may include generating recommendations to the patient or a clinician regarding pain treatment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

FIG. 1 illustrates, by way of example and not limitation, an example of a neuromodulation system 100 and portions of an environment in which the neuromodulation system 100 may operate. The system 100 is illustrated for implantation near the spinal cord, and can be configured to manage pain in a subject such as a patient with chronic pain. However, the neuromodulation system 100 may be configured to modulate other neural targets such as may be useful for delivering other therapies. The neuromodulation system 100 may include an implantable system 110 that may be associated with a body 199 of the subject, and an external system 130 in communication with the implantable system 110 via a communication link 120.

The implantable system 110 may include an ambulatory medical device (AMID), such as an implantable neuromodulator device (IND) 112, a lead system 114, and one or more electrodes 116. The IND 112 may be configured for subcutaneous implant in a patient's chest, abdomen, or other parts of the body 199. The IND 112 may be configured as a monitoring and diagnostic device. The IND 112 may include a hermetically sealed can that houses sensing circuitry to sense physiological or functional signals from the patient via sensing electrodes or ambulatory sensors associated with the patient and in communication with the IND 112. In some examples, the sensing electrodes or the ambulatory sensors may be included within the IND 112. Physiological or functional signals may be sensed during a pain episode. The sensed physiological or functional signals may include at least one signal indicative of muscle electrical or mechanical activity at a specific body location. The IND 112 may generate signal metrics indicative of muscle tension from the sensed muscle electrical or mechanical activity signal, and characterize and quantify the pain, such as to determine onset, intensity, severity, duration, or patterns of the pain experienced by the subject. The IND 112 may generate an alert to indicate occurrence of a pain episode, pain exacerbation, or efficacy of pain therapy, and present the alert to a clinician.

The IND 112 may alternatively be configured as a therapeutic device for treating or alleviating the pain. In addition to pain monitoring circuitry, the IND 112 may further include a therapy unit that can generate and deliver energy or modulation agents to a target tissue. The energy may include electrical, magnetic, or other types of energy. In some examples, the IND 112 may include a drug delivery system such as a drug infusion pump that can deliver pain medication to the patient, such as morphine sulfate or ziconotide, among others.

The IND 112 may include electrostimulation circuitry that generates electrostimulation pulses to stimulate a neural target via the electrodes 116 operably connected to the IND 112. In an example, the electrodes 116 may be positioned on or near a spinal cord, and the electrostimulation circuitry may be configured to deliver SCS to treat pain. In another example, the electrodes 116 may be surgically placed at other neural targets such as a brain or a peripheral neutral tissue, and the electrostimulation circuitry may be configured to deliver brain or peripheral stimulations. Examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic nerve modulation, adrenal gland modulation, baroreceptor stimulation, or transcranial magnetic stimulation, spinal cord stimulation (SCS), dorsal root ganglia (DRG) stimulation, motor cortex stimulation (MCS), transcranial direct current stimulation (tDCS), transcutaneous spinal direct current stimulation (tsDCS), pudendal nerve stimulation, multifidus muscle stimulation, transcutaneous electrical nerve stimulation (TENS), tibial nerve stimulation, among other peripheral nerve or organ stimulation. The IND 112 may additionally or alternatively provide therapies such as radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, or nerve blocks or injections.

In various examples, the electrodes 116 may be distributed in one or more leads of the lead system 114 electrically coupled to the IND 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IND 112 and tissue of the patient. The neurostimulation pulses are each delivered from the IND 112 through a set of electrodes selected from the electrodes 116. In various examples, the neurostimulation pulses may include one or more individually defined pulses, and the set of electrodes may be individually definable by the user for each of the individually defined pulses.

Although the discussion herein with regard to the neuromodulation system 100 focuses on implantable device such as the IND 112, this is meant only by way of example and not limitation. It is within the contemplation of the present inventors and within the scope of this document, that the systems, devices, and methods discussed herein may also be used for pain management via subcutaneous medical devices, wearable medical devices (e.g., wrist watch, patches, garment- or shoe-mounted device, etc.), or other external medical devices, or a combination of implantable, wearable, or other external devices. The therapy, such as electrostimulation or medical therapies, may be used to treat various neurological disorders other than pain, which by way of example and not limitation may include epilepsy, obsessive compulsive disorder, tremor, Parkinson's disease, or dystonia, among other movement and affective disorders.

The external system 130 may be communicated with the IND 112 via a communication link 120. The external system 130 may include a dedicated hardware/software system such as a programmer, a remote server-based patient management system, or alternatively a system defined predominantly by software running on a standard personal computer. The external system 130 may be configured to control the operation of the IND 112, such as to program the IND 112 for delivering neuromodulation therapy. The external system 130 may additionally receive via the communication link 120 information acquired by IND 112, such as one or more sensor signals. In an example, the external system 130 may program the IND 112 to deliver pain therapy in a closed-loop fashion based on the signals received from the IND 112. The external system 130 may include a display configured to display information including, for example, signal received by the IND 112, a pain or paresthesia map indicating pain or paresthesia perception at various body locations of the patient, programming of pain therapy such as a stimulation setting including parameters and their values, among others. In some examples, the external system 130 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

The communication link 120 may include one or more communication channels and intermediate devices between the external system and the IND 112. In an example, the communication link 120 may be a wired connection. In another example, the communication link 120 may be a wireless link, such as an inductive telemetry link, a capacitive telemetry link, a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible. In an example where the external system 131) includes a remote server such as configured as a uni-, multi- or distributed computing and processing system, the network 122 may be based on the Transmission Control Protocol/Internet Protocol (TCP/IP) network communication specification, although other types or combinations of networking implementations are possible. Similarly, other network topologies and arrangements are possible.

The communication link 120 may provide for data transmission between the IND 112 and the external system 130. The transmitted data may include, for example, real-time sensor signals acquired by and stored in the IND 112, therapy history data, data indicating device operational status of the IND 112, one or more programming instructions to the IND 112 which may include configurations for sensing physiologic signal or stimulation commands and stimulation parameters, or device self-diagnostic test, among others. In some examples, the IND 112 may be coupled to the external system 130 further via an intermediate control device, such as a handheld external remote control device to remotely instruct the IND 112 to generate electrical stimulation pulses in accordance with selected stimulation parameters produced by the external system 130.

Portions of the IND 112 or the external system 130 may be implemented using hardware, software, firmware, or combinations thereof. Portions of the IND 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

The neuromodulation system 100 may include a programming aid device (PAD) 140 operable by a patient. The PAD 140 may be a personal mobile electronic device, such as a smart phone, a smart watch, a smart wristband, a laptop computer, a tablet, among other mobile electronic devices holdable or wearable by the patient. The PAD 140 may be communicatively coupled to the IND 112, and control the operation of the IND 112. In an example, the PAD 140 may include a user interface that allows a user to program the IND 112 to deliver a neuromodulation therapy. Unlike the external system 130 which generally includes devices operated by a healthcare provider or an authorized device operator other than the patient, the PAD 140 may be configured to be operated by the patient to evaluate his/her pain or paresthesia perception, and adjust pain therapy via the IND 112. As illustrated in the FIG. 1, the PAD 114 may communicate with the IND 112 (e.g., to adjust therapy) directly via a communication link 190. Alternatively, the PAD 114 may communicate with the IND 112 indirectly through the external system 130.

The PAD 140 may include a communication module, such as a transceiver circuit, to establish data communication with one or more user assistive devices 150 and a remote computing device 160, such via wireless network connections 180. The one or more user assistive devices 150 may be operated respectively by one or more human assistants including, for example, a medical professional, a caregiver, or a device manufacturer representative. The remote computing device 160 may implement a software-based virtual agent (SVA) configured to assist or guide the patient in pain or paresthesia assessment, and pain management such as programming the implantable system 110. In an example, the remote computing device 160 can be a cloud-computing device or networked devices. The PAD 140 may implement and run a remotely-accessible pain management platform that enables multi-party information exchange among the patient, the SVA, and one or more human assistants, with regard to patient pain or paresthesia perception, individualized pain therapy, device integrity testing or trouble-shooting, among other functionalities, examples of which are described below with respect to FIGS. 3-9.

Figure 2:
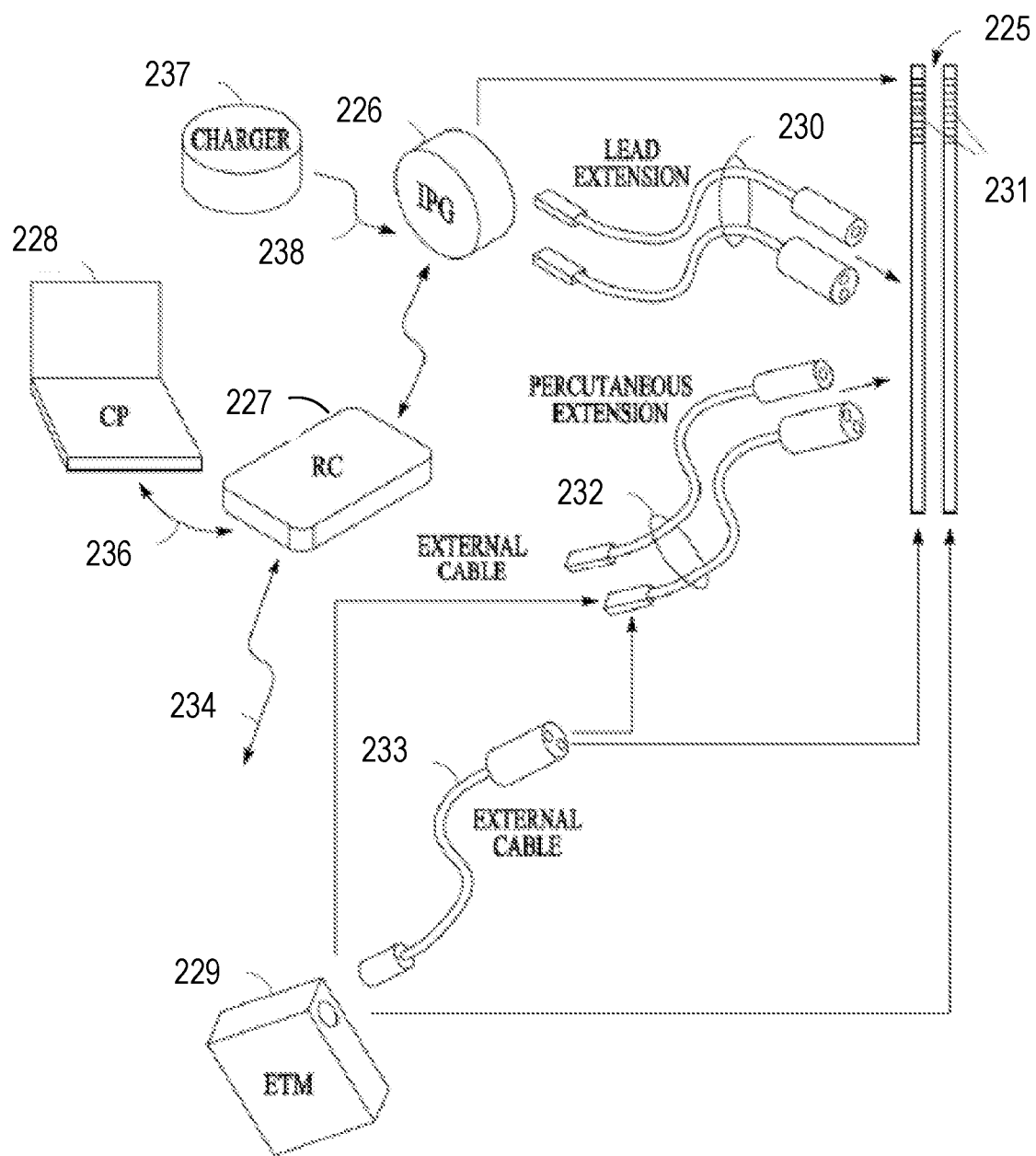
FIG. 2 illustrates, by way of example, an example of a SCS system.

FIG. 2 illustrates, by way of example, an example of a SCS system 200, which also may be referred to as a Spinal Cord Neuromodulation system. The SCS system 200, which is an example of the implantable system 110, may generally include a plurality (illustrated as two) of implantable neuromodulation leads 225, an implantable pulse generator (IPG) 226, an external remote controller RC 227, a clinician's programmer (CP) 228, and an external trial modulator (ETM) 229. The IPG 226 may be physically connected via one or more percutaneous lead extensions 230 to the neuromodulation leads 225, which carry a plurality of electrodes 231. As illustrated, the neuromodulation leads 225 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 226 includes pulse generation circuitry, also referred to as a pulse generator, that delivers electrical neuromodulation energy in the form of a pulsed electrical waveform (i.e., a temporal series of electrical pulses) to the electrodes in accordance with a set of neuromodulation parameters.

The ETM 229 may also be physically connected via the percutaneous lead extensions 232 and external cable 233 to the neuromodulation leads 225. The ETM 229 may have similar pulse generation circuitry as the IPG 226 to deliver electrical neuromodulation energy to the electrodes in accordance with a set of neuromodulation parameters. The ETM 229 is a non-implantable device that is used on a trial basis after the neuromodulation leads 225 have been implanted and prior to implantation of the IPG 226, to test the responsiveness of the neuromodulation that is to be provided. Functions described herein with respect to the IPG 226 can likewise be performed with respect to the ETM 229.

The RC 227 may be used to telemetrically control the ETM 229 via a bi-directional RF communications link 234. The RC 227 may be used to telemetrically control the IPG 226 via a bi-directional RF communications link 235. Such control allows the IPG 226 to be turned on or off and to be programmed with different neuromodulation parameter sets. The IPG 226 may also be operated to modify the programmed neuromodulation parameters to actively control the characteristics of the electrical neuromodulation energy output by the IPG 226. A clinician may use the CP 228 to program neuromodulation parameters into the IPG 226 and ETM 229 in the operating room and in follow-up sessions.

The CP 228 may indirectly communicate with the IPG 226 or ETM 229, through the RC 227, via an IR communications link 236 or another link. The CP 228 may directly communicate with the IPG 226 or ETM 229 via an RF communications link or other link (not shown). The clinician detailed neuromodulation parameters provided by the CP 228 may also be used to program the RC 227, so that the neuromodulation parameters can be subsequently modified by operation of the RC 227 in a stand-alone mode (i.e., without the assistance of the CP 228). Various devices may function as the CP 228. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 228. Alternatively, such programming methodologies can be performed using firmware or hardware. In any event, the CP 228 may actively control the characteristics of the electrical neuromodulation generated by the IPG 226 to allow the desired parameters to be determined based on patient feedback or other feedback and for subsequently programming the IPG 226 with the desired neuromodulation parameters. To allow the user to perform these functions, the CP 228 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical neuromodulation energy output by the neuromodulation leads, and select and program the IPG with neuromodulation parameters in a surgical or clinical setting.

An external charger 237 may be a portable device used to transcutaneously charge the IPG via a wireless link such as an inductive link 238. Once the IPG has been programmed, and its power source has been charged by the external charger or otherwise replenished, the IPG may function as programmed without the RC or CP being present.

Figure 3:
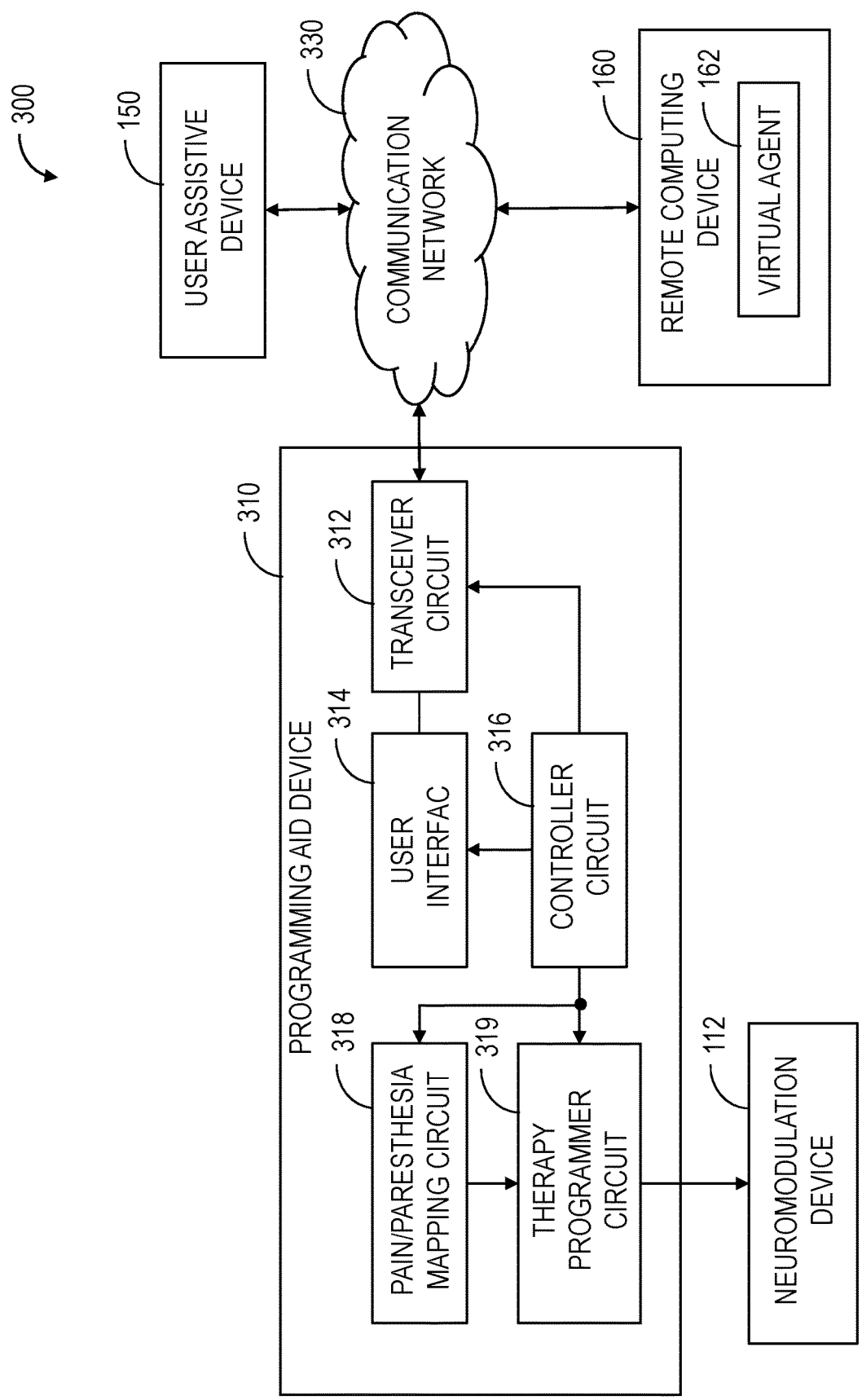
FIG. 3 is a block diagram illustrating an example of a computer-assisted pain mapping and neuromodulation system, which is an example of the neuromodulation system as shown in FIG. 1.

FIG. 3 illustrates a block diagram illustrating an example of a computer-assisted pain mapping and neuromodulation system 300, which is an example of the neuromodulation system 100. The system 300 may establish information exchange between a patient and one or more of a software-based virtual agent (SVA) or a human assistant on a remotely-accessible pain management platform, evaluate patient pain or paresthesia, and/or program a neuromodulation therapy based on the information exchange to treat chronic pain or other disorders.

The system 300 may include a programming aid device (PAD) 310 communicatively coupled to one or more of a user assistive device 150 or a remote computing device 160 via a communication network 330 providing Internet connections. The PAD 310, which is an example of the PAD 140 as shown in FIG. 1, can be a mobile electronic device holdable or wearable by the patient. In an example, the PAD 310 may be an off-the-shelf, commercially available consumer electronic device, such as a smart phone, a smart watch, a smart wristband, a laptop computer, a tablet, among other mobile electronic devices. Such a commercially available consumer device may include infrastructures, circuitry, peripherals, firmware, and software to support information processing, storage, presentation, and transmission through a communication network.

The PAD 310 may include one or more of a transceiver circuit 312, a user interface 314, a controller circuit 316, a pain or paresthesia mapping circuit 318, and a therapy programmer circuit 319. In an example, the transceiver circuit 312 can be a part of the build-in communication circuitry of the PAD 310. In some examples, the transceiver circuit 312 can be an external device detachably attached to the PAD 310 through a wired connection or a wireless connection. The transceiver circuit 312 can be configured to facilitate communications between the PAD 310 and one or more of the user assistive device 150 or the remote computing device 160 via the communication network 330. The communication network 330 may include Internet, LAN (Local Area Network), Wireless LAN (Wireless Local Area Network), WAN (Wide Area Network), PAN (Personal Area Network), or the like. In an example where the PAD 310 is a smart phone, the transceiver circuit 312 may be connected to Internet via a cellular network, a WiFi network, or a physical connection such as Ethernet or modem, and transmit information to, and receive information from, the user assistive device 150 and/or the remote computing device 160. The user assistive device 150, as discussed above with reference to FIG. 1, may be operated by one or more human assistants including, for example, medical professionals, caregivers, or device experts such as device manufacturer representatives. Examples of the user assistive device 150 may include commercially available devices or purpose-build devices, such as a desktop personal computer, a laptop computer, or a mobile electronic device such as a smart phone, a smart watch, a smart wristband, a tablet, among others. The remote computing device 160, as discussed above with reference to FIG. 1, may be a cloud-computing device or networked devices.

The user interface 314 may include an input device configured to receive, from the patient, information about pain or paresthesia perception of the patient. The paresthesia may be induced by electrostimulation of a body site of the patient, such as provided by an implantable neuromodulator programmed to deliver neuromodulation energy to target tissue according to a stimulation setting via a set of electrodes at respective electrode locations. Examples of the target tissue may include a portion of a spinal cord, one or more spinal nerves, dorsal roots, or dorsal root ganglia. The stimulation setting may include a location of central point of stimulation (CPS) that represents a focal point of a stimulation field. The stimulation setting may additionally or alternatively include one or more stimulation parameters (also referred to as a neuromodulation parameter set). Examples of the stimulation parameters may include a current amplitude or a voltage amplitude, a pulse width, a pulse shape (waveform), a pulse rate, or a duty cycle, among other parameters.

The input device of the user interface 314 may enable the patient to input pain or paresthesia information using texts, graphs, images, audio, or video input. Examples of the input device may include keyboard, on-screen keyboard, mouse, trackball, touchpad, touch-screen, or other pointing or navigating devices. The patient input of the pain or paresthesia information may include an indication of one or more body locations where the pain or paresthesia perception is perceived, also referred to as pain or paresthesia sites. The patient input may additionally or alternatively include an indication of intensity of pain or paresthesia perception at a body site, or an indication of quality of the pain or paresthesia perception at a body site (e.g., a spatial distribution, or a temporal pattern, such as persistence, of pain or paresthesia), or type of pain (e.g., dull pain, sharp pain, aching, numbness, burning, stabbing, or needle pain) or type of paresthesia (e.g., tingling, numbness, skin crawling, or itching), among other pain or paresthesia perception information. In some examples, the user interface 314 may incorporate virtual reality (VR) technology (e.g., a mobile VR headset) or augmented reality (AR) technology (e.g., a mobile smart device displaying superimposed graphics or objects) to enhance patient's experience during assistive pain evaluation and pain management.

Figures 4, 5:
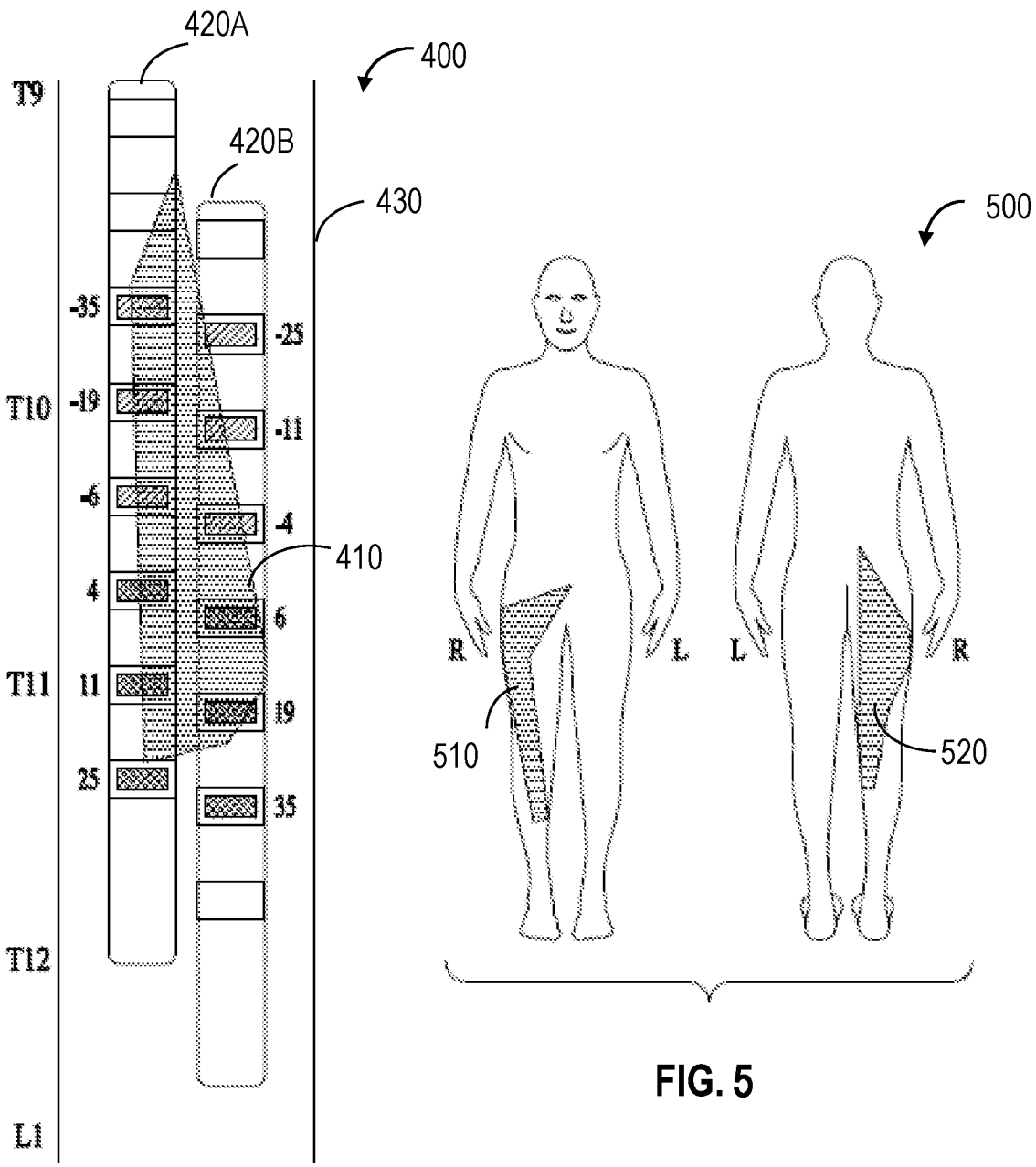
FIGS. 4-5 are diagrams illustrating, by way of example and not limitation, pain or paresthesia sites on a body, and their spatial relationship with implantable leads for delivering neuromodulation therapy.

The pain or paresthesia mapping circuit 318 may generate a pain/paranesthesia map by incorporating the patient input of the pain or paresthesia information into an auto-generated body surface map. In an example, the patient may use a tool (e.g., a stylus or other pointing device) or fingers to draw a pain or paresthesia map, or mark or label pain or paresthesia sites on the body surface map, on a touchscreen of the user interface. In some examples, the markings or labels include different symbols or annotations to distinguish different intensities, qualities, or types of pain or paresthesia perceptions. Referring now to FIGS. 4-5, the diagrams therein illustrate, by way of example and not limitation, areas on a patient body where pain is felt (pain sites) or where paresthesia is perceived responsive to electrostimulation (paresthesia sites), and their spatial relationship with implantable leads for delivering neuromodulation therapy. The pain or paresthesia sites may be identified and labeled by the patient (e.g., free-hand drawing), derived from a patient pain drawing or paresthesia drawing via a look up table or an algorithm, or using a combination of the methods thereof. FIG. 4 illustrates an example of a drawing 400 of paint/paresthesia sites 410 over a representation of electrode arrays on respective implantable leads 420A-420B implanted in target body sites 430. The implantable leads 420A-420B, which are examples of the leads 231 as illustrated in FIG. 2, may be configured to deliver electrostimulation to target sites 430 on or near a spinal cord. The target sites 430 may be pain sites (in which case the drawing 400 is referred to as a pain drawing), or paresthesia sites (in which case the drawing 400 is referred to a paresthesia drawing). FIG. 5 illustrates, by way of example and not limitation, a drawing 500 representing pain or paresthesia sites on a body surface map including ventral and dorsal depictions of the body. In the illustrated example, the pain or paresthesia sites are marked in a first drawing 510 on a ventral depiction of the body, and in a second drawing 520 on a dorsal depiction of the body. In some examples, separate pain drawings and paresthesia drawings may be generated, and provided to a neuromodulation control system to generate an indication of spatial correspondence between the pain sites and the paresthesia sites.

Figure 6:
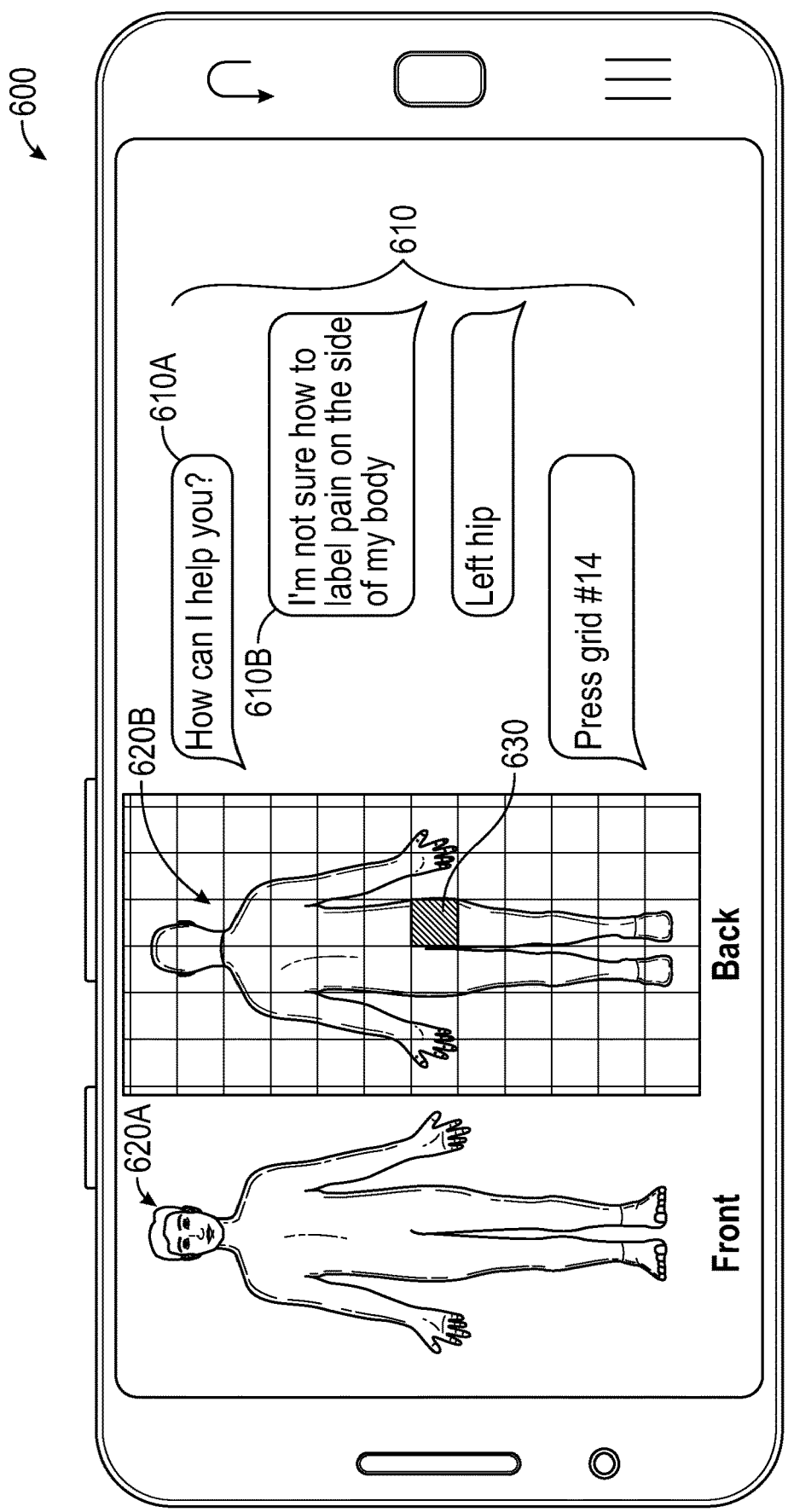
FIGS. 6-8 are diagrams illustrating, by way of example and not limitation, screenshots of information exchange sessions between the patient and an SVA and/or a human assistant regarding pain or paresthesia perception and pain management.

In addition to or as an alternative of the pain or paresthesia drawings 510 and 520, in some examples, a gridded body surface map may be provided to the patient, which may include spatially-indexed grid cells covering the entirety or a portion of the body surface map. To identify the pain or paresthesia sites, the patient may select one or more grid cells from the gridded body surface map that correspond to the pain or paranesthesia sites, examples of which are illustrated in FIG. 6.

The pain or paresthesia mapping circuit 318 may map the patient identified pain or paresthesia to various skin areas corresponding to spinal nerves that innervate those skin areas, also known as dermatome compartments. The mapping may be a point-by-point mapping via a look-up table or a dictionary/key system. The center, length, and width of the target linear field may be determined based on the spatial extent of the spinal cord region corresponding to the patient's reported pain region. A clinician or other specialist, a patient or a combination of persons may work together to highlight region of spinal cord and/or body where they want stimulation to be targeted (i.e. focus stimulation on anatomical correlate and/or reported site of pain). Internal look-up table and/or inverse algorithm with field "primitives" tied to specific regions/region sizes may be used to display and configure electrode settings according to this anatomically-based specification. The neuromodulation system may determine an optimal stimulation setting, such as a stimulation field definition or current or energy fractionalization among electrodes based on the pain mapping.

The pain or paresthesia information provided by the patient, including pain/paranesthesia map with labeling of the identified pain or paresthesia sites, optionally along with patient input of intensity, quality, type of pain or paresthesia at respective sites, may be presented to the user on an output device of the user interface 314. The information may be displayed on a display unit in texts, graphs, images, table, charts, diagrams, among other formats. In some examples, the output device may additionally or alternatively present the information in an audio or video format. In some examples, the output device may generate alerts, alarms, emergency calls, or other forms of warnings to the patient regarding pain mapping or pain therapy.

The transceiver circuit 312 may receive information regarding pain sensation and pain management of the patient provided by one or more parties including, for example, one or more human assistants via one or more user assistive devices 150, and/or a software-based virtual agent (SVA) 162 implemented in an executed by the remote computing device 160. In an example, the SVA 162 may be a chatbot configured to interact with the patient through verbal communications such as conversational messages, emails, voices, or visual (e.g., images or video) formats of information exchange. The SVA 162 may be a software program that uses one or more of scripted rules, artificial intelligence (AI) applications, machine learning (ML) algorithms, or natural language processing and understanding applications, to interpret and discern patient descriptions and requests, and provide the patient with automated service and guidance for pain or paresthesia assessment, localization (i.e., identifying pain or paresthesia sites), characterization, diagnostics, and programming a neuromodulation therapy via the PAD 310 and the IND 112. With the built-in AI and ML capabilities, the SVA 162 may be trained to understand patient intent and provide personalized answers or suggestions in a humanlike manner. For example, the SVA 162 may fine-tune and expand its language understanding system to better interpret and respond to the patient's inquiries and requests. The AI and ML capabilities may also enable the SVA 162 to acquire knowledge and learn from inputs provided by the human assistant (e.g., clinicians, caregivers, or device experts). For example, as to be discussed in the following, the human assistant may confirm, override, or modify the pain parameter settings suggested by the SVA 162. Based on input of the human assistant, the SVA 162 may update its reasoning and decision-making system to adapt to individual patient condition, thereby enhancing its performance of assisting the patient in pain evaluation and individualized pain management.

To take the advantage of the assistance provided by the SVA 162 or a human assistant, the controller circuit 316 may establish a remotely-accessible pain management platform that enables multi-party information exchange among the patient, the SVA 162, and one or more human assistants, with regard to patient pain or paresthesia perception, individualized pain therapy, device integrity testing or trouble-shooting, among other functionalities. In an example, the pain management platform is a software application ("app") installed and run on the PAD 310. The controller circuit 316, responsive to a patient command, may initiate and manage an information exchange session between the patient and the SVA 162, and/or one or more human assistants regarding patient pain or paresthesia perception and pain management. The exchanged information may be presented on the user interface 314 as texts, graphs, images, audio, or video format. In an example, the exchanged information may include information about mapping pain or paresthesia perception onto a body surface map. In another example, the exchanged information may include information about configuring a neuromodulation device, such as the IND 112, to deliver a pain therapy. The configuration of the neuromodulation device may include operations to be taken by the patient to program or adjust a stimulation setting, as suggested by the SVA 162 or one or more human assistants. In yet another example, the exchanged information may include information about integrity testing or trouble-shooting of the neuromodulation device, such as checking battery status, connections among components such as the leads 225, an IPG 226, the RC 227, the CP 228, the ETM 229, as shown in FIG. 2. The controller circuit 316 may perform device integrity testing or trouble-shooting based on the exchanged information. In some examples, the device integrity testing or trouble-shooting may be performed by the SVA 162 automatically at a scheduled time, periodically at a specified frequency, or triggered by a patient request or other events. In some examples, the controller circuit 316 may track the information exchange sessions over time, and store the information exchange sessions in a storage device. Examples of the multi-party information exchange for pain or paresthesia assessment and pain management are discussed below, such as with reference to FIGS. 6-9.

Based on the information exchange regarding pain or paresthesia assessment (e.g., pain or paresthesia sites, intensity, quality, type, etc.), the controller circuit 316 may determine a stimulation setting for the neuromodulation device. The therapy programmer circuit 319 may program the neuromodulation device 112 to initiate or adjust a pain therapy in accordance with the suggested stimulation setting. The stimulation setting may include an electrode configurations, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include amplitude, pulse width, rate (or frequency), or waveform of the electrical pulses. Each electrode configuration, along with the electrical pulse parameters, can be referred to as a "neuromodulation parameter set." Each set of neuromodulation parameters, including fractionalized current distribution to the electrodes (as percentage cathodic current, percentage anodic current, or off), may be stored and combined into a neuromodulation program that can then be used to modulate multiple regions within the patient.

In an example, the controller circuit 316 may determine a stimulation setting by first determining an optimal stimulation field definition, which includes field size, shape, intensity, field scaling and steering parameters, among other parameters. Based on a pain targeting metric (PTM) representing a spatial correspondence between the pain perception and the paresthesia responsive to diagnostic electrostimulation, the controller circuit 316 may determine for each electrode a corresponding anodic weight and a cathodic weight. The electrode has a net anode effect if the anodic weight is greater than the cathodic weight, or a net cathode effect if the anodic weight is less than the cathodic weight. A normalization factor may be applied to control a relative strength (proportion) of the anode effect or cathode effect distributed to that electrode. The normalization factors of all the electrodes with a net anode effect add up to 100%. The normalization factors of all the electrodes with a net cathode effect add up to −100%.

Based on the optimal stimulation field definition, the controller circuit 316 may regulate neuromodulation energy (e.g., electrical current) to individual ones of a set of electrodes, a process referred to as energy or current fractionalization among electrodes, or fractionalized electrode configuration. In an example, the controller circuit 316 may determine current fractionalization among multiple electrodes in accordance with an objective function. An objective function refers to a function with desirable characteristics for modulating the targeted tissue. The objective function may also be referred to as an objective target function. An objective function for a broad and uniform modulation field is identified for a given volume of tissue. Examples of an objective function includes a constant E (electric field), a constant |E| (electric field magnitude), and a constant voltage. Information such as lead and electrode configuration, electrode tissue coupling, electrode contact status, and a threshold such as a current threshold, may be used as input to an electrode energy fractionalizer that regulates electrical current to individual electrodes based on the stimulation field definition. A function can be performed that is dependent on the objective function, the electrode positions, and the electrode tissue coupling. The result of the function is the fractionalization of modulation energy (e.g. current) for each electrode to achieve the objective function. The fractionalization of modulation energy may be expressed, for each electrode, as a polarity and percentage of the total cathodic energy (add up to 100%) or percentage of total anodic energy (add up to −100%) delivered to the plurality of electrodes on the lead at a given time. Furthermore, an amplitude boost or scaling factor may be applied to the fractionalization values. In some examples, a selected field model may be used to estimate the field induced by unit current from the contact. The field is calibrated using the threshold. Constituent forces are formed based on the selected contacts. A transfer matrix (A) may be constructed, which mathematically describe the electrical behavior of the model. A specified target stimulation field may be provided to the model. The target stimulation field ((p) can be represented by a central point of stimulation (CPS). The transfer matrix (A) can be used to compute the minimal mean square solution using contributions from the constituent sources and the specified target field. The solution can be used to compute the current fractionalization on each contact. Electrodes configured in accordance with the current fractionalization may be used to establish a stimulation field to modulate target neural element for pain relief.

In various examples, one or more of the pain or paresthesia mapping circuit 318 or the therapy programmer circuit 319, optional among other components of the PAD 310, may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a processor that may receive and execute a set of instructions of performing the functions, methods, or techniques described herein.

Figure 7:
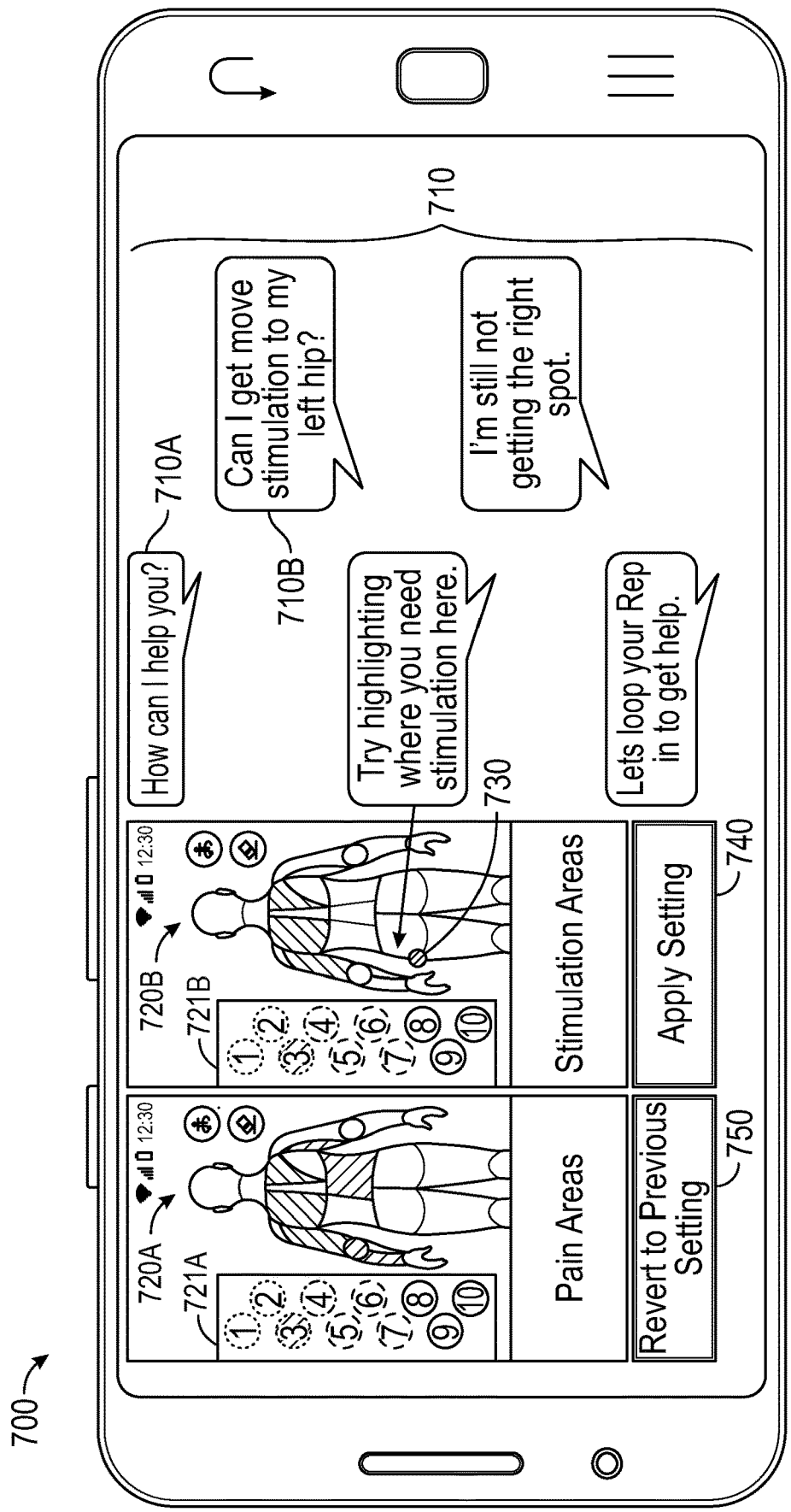
Figure 8:
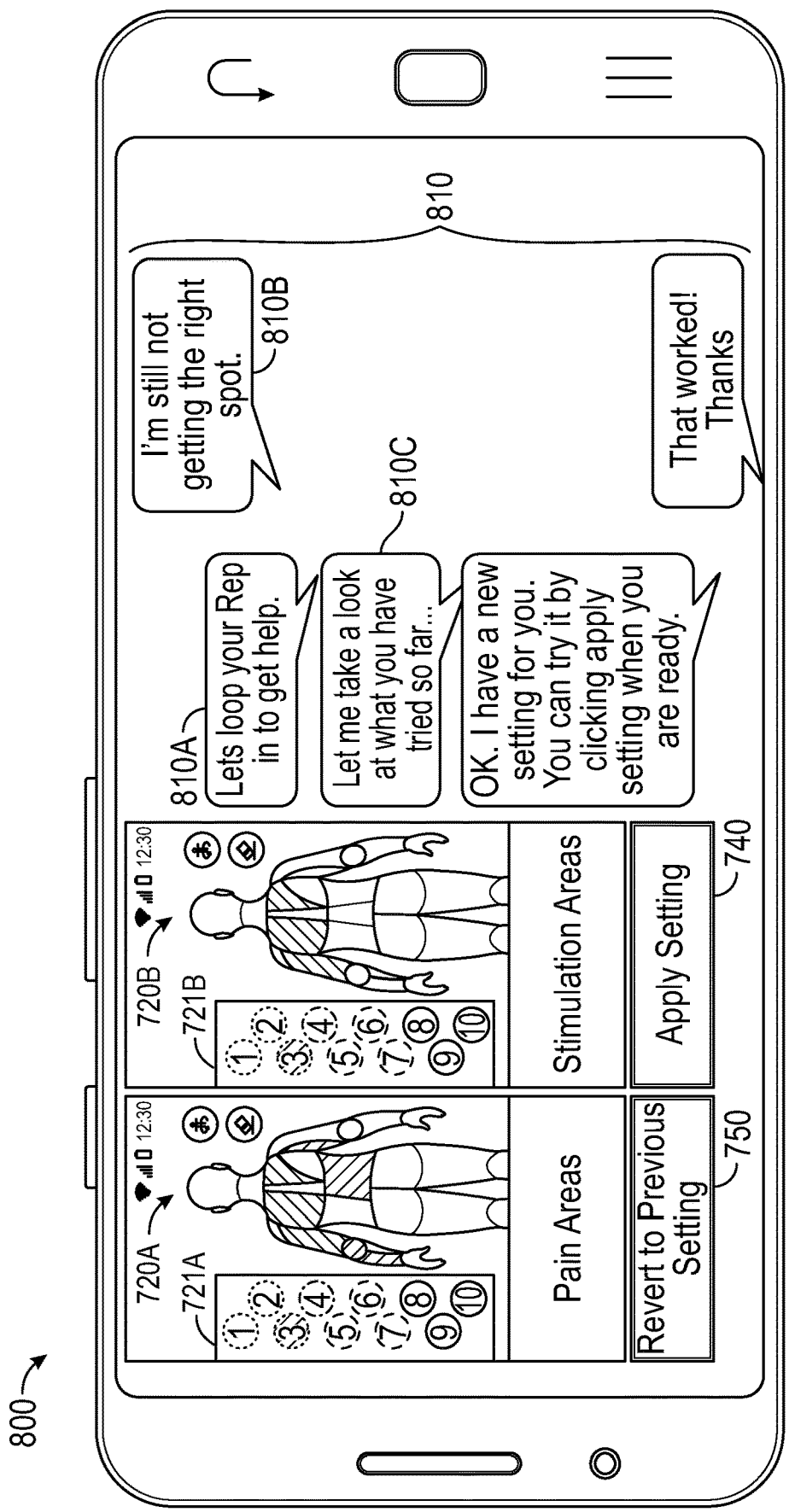

FIGS. 6-8 are diagrams illustrating, by way of non-limiting example, sessions of multi-party information exchange between the patient and the SVA 162 and/or one or more human assistants regarding patient pain or paresthesia assessment and pain management. Such information exchanges sessions may be managed by the controller circuit 316. The SVA 162 and/or a human assistant may aid, guidance, or suggestions for mapping patient pain or paresthesia perceptions, programing or adjusting a pain therapy, or integrity testing and trouble-shooting of the neuromodulation device, among other services. In some examples, the patient may request clarification of the guidance or suggestions on the part of the SVA 162 or the one or more human assistants. The information exchange session may be carried out on a user interface of the PAD 310, which in this example is a smart phone. Although textual messages are shown in the examples illustrated in FIGS. 6-8, other formats such as audio or video messages have also been contemplated. The information exchange session may be initiated by the patient, such as by running the mobile "app" on a smart phone. The parties may log into the pain management platform and establish communications between the PAD 310 and the remote computing device 160 and/or the user assistive device 150. The SVA 162 and/or one or more human assistants may automatically join the information exchange session, or upon a request by the patient. In some examples, one or more human assistants may join the information exchange session upon a request by the SVA 162.

FIG. 6 illustrates an example of a screenshot 600 of the user interface of the PAD 310 on the patient end that shows, among other things, textual messages 610 exchanged between the patient and the SVA 162 regarding mapping patient pain or paresthesia perception onto a body surface map. The textual messages 610 include incoming messages 610A received from the SVA 162, and outgoing messages 610B sent by the patient to the SVA 162. In the example as illustrated, the body surface map includes a ventral (front) view 620A and a dorsal (back) view 620B of the body. One or both of views 620A-620B may be represented by a gridded body surface map. The gridded body surface map, such as shown in 620B, includes spatially-indexed grid cells covering the entirety or a portion of the body surface map. The SVA 162 may interpret and discern patient description about the pain or paresthesia perception (e.g., locations, and optionally intensity or type), and guide the patient to identify pain or paresthesia sites, such as by informing the patient appropriate grid cell(s) 630 on the gridded body surface map that corresponds to patient description of pain or paranesthesia sites. The patient may then mark such identified grid cells on the gridded body surface map. Additional information about the pain or paresthesia perception at the identified grid cells, such as intensity, quality, type of pain or paresthesia, may be added to the gridded body surface map.

FIG. 7 illustrates an example of a screenshot 700 of the user interface of the PAD 310 on the patient end that shows, among other things, textual messages 710 exchanged between the patient and the SVA 162 regarding programming the neuromodulation device 112 to initiate or adjust a pain therapy. The textual messages 710 include incoming messages 710A received from the SVA 162 and outgoing messages 710B sent by the patient to the SVA 162. In this example, a pain map 720A may be provided to illustrate pain areas on the body. The patient may modify the pain map 720A by, for example, identifying newly experienced pain areas (such as through an information exchange session for pain mapping, as illustrated in FIG. 6), or specifying or changing other pain information (e.g., intensity, quality, or type of pain) at a previously identified pain site or a newly identified pain site. In an example, a panel of markers 721A representing categorized pain information, such as different pain intensity levels, may be shown next to the pain map 720A. The pain intensity levels may be represented by numerical values, such as from 1 to 10, where a smaller number represents a lower pain intensity level, and a larger number represents a higher pain intensity level. The pain intensity levels may additionally or alternatively be color-coded, where, for example, a lower pain intensity level is colored green, and a higher pain intensity is colored red. Other visual identifiers (e.g., shading, patterns, shapes, or symbols) may be used to distinguish different pain intensity levels. The patient may use the panel of markers 721A to mark various pain locations with appropriate numerical values, color codes, or visual identifiers representing the pain intensities perceived at corresponding locations. The resulting pain map 720A, with pain coverage and pain intensities, may be shared with the SVA 162.

A stimulation map 720B may be provided to illustrate a plurality of stimulation areas representing the body areas where the pain therapy is currently actively applied. The patient may modify the stimulation map 720B by, for example, identifying one or more stimulation areas where electrostimulation treatment is desirable, or to be withheld or otherwise adjusted. In the example as illustrated, the patient requests (such as in a form of textual messages in this example) assistance for adjusting electrostimulation at a particular stimulation area (e.g., enhancing stimulation strength at left hip). The SVA 162 may interpret patient description and request, and guide the patient to label or mark, on the stimulation map 720B, a target stimulation area 730 to apply modified stimulation. A panel of markers 721B representing stimulation intensity or energy levels, may be shown next to the stimulation map 720B. The stimulation intensity or energy levels may be represented by numerical values, such as from 1 to 10, where a smaller number represents a lower stimulation intensity or energy level, and a larger number represents a higher stimulation intensity or energy level. The stimulation intensity or energy levels may additionally or alternatively be color-coded, where, for example, a lower stimulation intensity or energy level is colored green, and a higher stimulation intensity or energy is colored red. Other visual identifiers (e.g., shading, patterns, shapes, or symbols) may be used to distinguish different stimulation intensity or energy levels. The patient may use the panel of markers 721B to mark the identified stimulation areas (such as stimulation area 730 as shown) with appropriate numerical values, color codes, or visual identifiers representing stimulation intensity or energy levels to be applied thereto. The resulting stimulation map 720B, with stimulation coverage and stimulation intensities, may be shared with the SVA 162.

A new stimulation setting may be generated by the controller circuit 316 based on the identified stimulation area 730. To accept the new stimulation setting, the patient may click on or tap on the "Apply Setting" on-screen button 740. The therapy programmer circuit 319 may program the neuromodulation device to deliver stimulation in accordance with the new stimulation setting. In some examples, the patient may provide feedback (such as in a form of textual messages in this example) to the SVA 162. The patient may terminate the stimulation in accordance with the new setting, and revert to the previous setting, such as by clicking on or tapping on the "Revert to Previous Setting" on-screen button 750.

FIG. 8 illustrates an example of a screenshot 800 of the user interface of the PAD 310 on the patient end showing, among other things, textual messages 810 exchanged among the patient, the SVA 162, and a human assistant regarding programming the neuromodulation device 112 to initiate or adjust a pain therapy. The controller circuit 316 may generate an alert that can be sent to the user assistive device 150 to invite the human assistant to join an existing information exchange session in response to a request by the patient or the SVA 162. Additionally or alternatively, the controller circuit 316 may generate an alert that can sent to the user assistive device 150 to invite the human assistant to join the information exchange session in response to a trigger event. Examples of such a trigger event may include an identification of a new pain or paresthesia site identified by the patient, a new stimulation setting different from the existing stimulation setting and suggested by the SVA or requested by the patient, a frequent reprogramming of therapy exceeding a threshold, the SA recommending a tighter parameter guard rails, or an outlier event during programming of therapy, among others. Responsive to the trigger event, the human assistant is alerted to participate in the information exchange session. As illustrated in FIG. 8, the textual messages 810 include incoming messages 810A received from the SVA 162, outgoing messages 810B sent by the patient and directed to the SVA 162 or the human assistant, and incoming messages 810C from a human assistant. In some examples, the SVA 162 may screen the historical information exchange sessions stored in a storage device for any signs of a change in patient health status or emotion (e.g., distress, self-harm, complaints, device operation issues), and alert the human assistant about such signs. In some examples, the SVA 162 may generate a report for a human assistant to review. The report may be generated periodically at specified time, duration, or frequency, or in a commanded mode upon patient request, or in response to a trigger event as discussed above.

The screenshot 800 may similarly include one or more of the pain map 720A and the stimulation map 720B, and panels of markers 721A and 721B representing respectively pain intensity levels and stimulation intensity or energy levels that may be used by the patient to create or modify respectively the pain map 720A and the stimulation map 720B, as discussed above with respect to FIG. 7. In this example, the pain map 720A and the stimulation map 720B may be shared with the SVA 162 and the human assistant.

In some examples, the controller circuit 316 may apply a hierarchical order to determine an operation of the neuromodulation device 112. For example, with regard to therapy adjustment, while the patient may be authorized to self-program the neuromodulation device 112, such a function may be disabled by the SVA 162 or a human assistant. In another example, a human assistant, when joining an information exchange session, may confirm, override, or modify a stimulation setting suggested by the SVA 162. In some examples, the SVA 162 may learn from inputs from the human assistant, and update its reasoning and decision-making system. The confirmation, override, or confirmation may be executed automatically. Alternatively, the patient or the SVA 162 may request a human assistant's authorization for therapy adjustment. In the interim prior to such an authorization, the SVA 162 may give the patient an option to proceed with the patient's other requests in the present information exchange session other than the authorized therapy change, such as pain or paresthesia evaluation, or device integrity testing or trouble-shooting. The therapy programmer circuit 319 may program the neuromodulation device 112 to deliver the pain therapy in accordance with the new stimulation setting upon the human assistant's confirmation of said stimulation setting.

The controller circuit 316 may set limits on permissions or rights of access for various parties participating in the information session, including the patient, the SVA 162, and/or one or more human assistants. Each party has a role that defines a specific set of permitted and/or prohibited actions that the party can take. For example, the patient's role may include initiating a session, connecting to the SVA 162 or a human assistant, granting permission to a device manufacturer representative to take control of programming the neuromodulation device 112, self-programming the neuromodulation device 112 (if the human assistant has not locked the patient out of that feature), naming the session, scheduling the information sessions or device check such as based on a time of day, among others. The clinician's role may include assigning or modifying therapies, requiring the patient to utilize other human assistant such as a device manufacturer representative to assist in programming a therapy, or setting or changing a safety limit. The device manufacturer representative's role may include assigning patients to clinician, confirming or overriding or modifying a therapy setting proposed by the SVA 162, viewing proprietary device information not visible to the clinician or the patient, or setting safety limits, etc. Other human assistants, such as clinical researchers, administrative personnel, or other caretakers may have their respective roles, such as locking or unlocking certain features or settings for device programming. In an example, the controller circuit 316 may generate a control signal that gives permission to a clinician to make changes to a safety setting, such as a limit of a device parameter (e.g., limit of electrostimulation pulse amplitude), while prohibiting the patient and/or the SVA 162 to make such changes alone.

Figure 9:
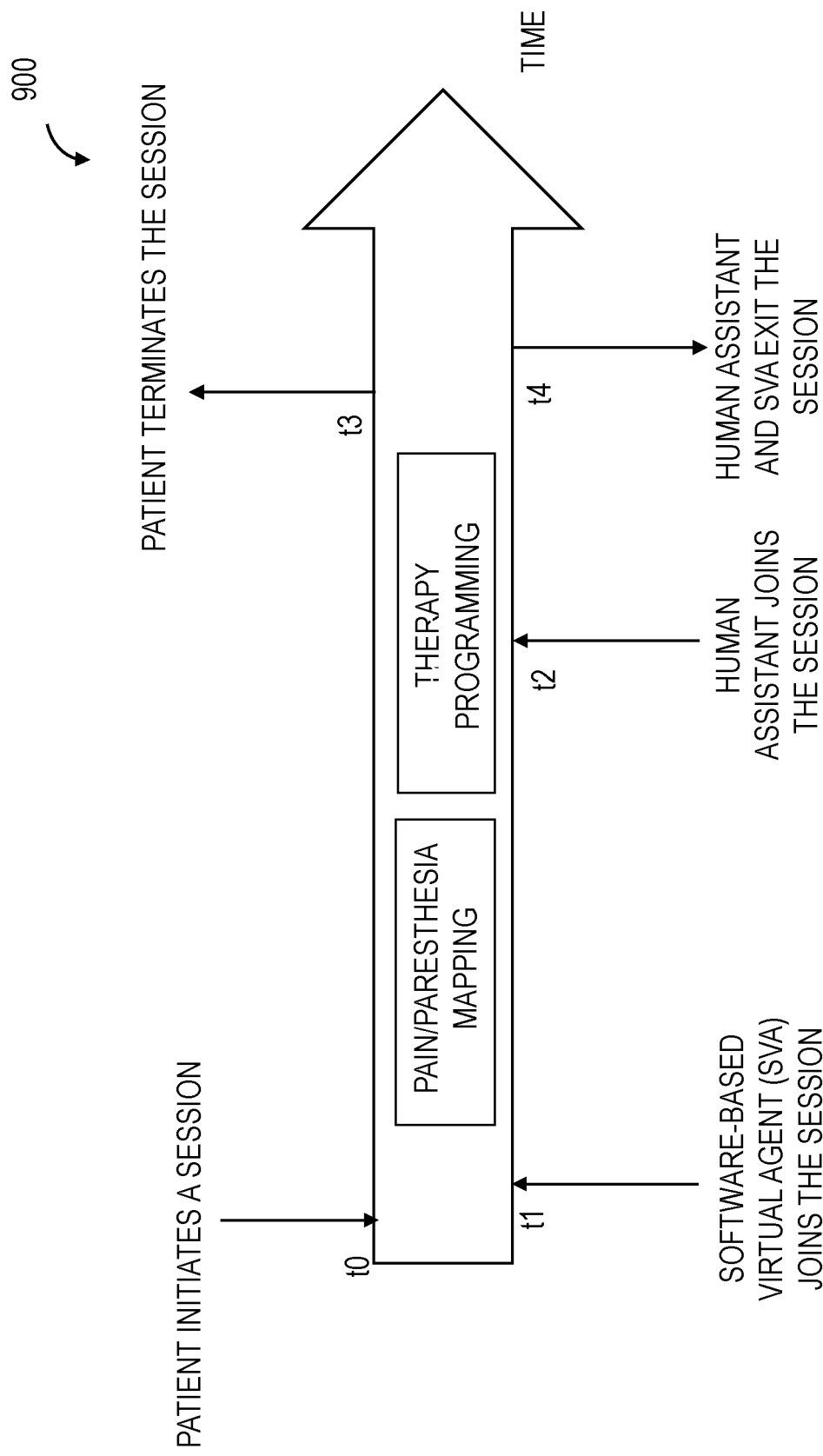
FIG. 9 is a timing diagram illustrating, by way of example, timings of events and party participation in an information exchange session.

FIG. 9 is a timing diagram 900 illustrating, by way of example, timings of events and party participation in an information exchange session. At t0, a patient logs into the pain management platform via the PAD 140 or the PAD 310, such as by running a mobile "app" on a smart phone, to initiate an information exchange session. At t1, the SVA 162 may join the session remotely from the remote computing device 160, either automatically or upon a request by the patient. Information regarding pain or paresthesia mapping may be exchanged between the patient and the SVA 162. Additionally or alternatively, information regarding therapy programming may be exchanged between the patient and the SVA 162. The pain or paresthesia mapping and therapy programming, although included in the same session in this example, may alternatively be split into two separate information exchange sessions. At t2, a human assistant may join the session, such as upon request by the SVA 162 or the patient, or automatically triggered by an event, as discussed above with reference to FIG. 8. The human assistant may assist the patient in programming a pain therapy, such as to confirm, override, or modify a programming setting suggested by the SVA 162. The patient may choose to apply the stimulation setting that has been confirmed or modified by the human assistant to the neuromodulation device to deliver a pain therapy. Then, the patient can terminate the session at t3, and the SVA 162 and the human assistant may exit the session at t4.

It is to be noted that the parties participating in the information exchange session, their respective timings of participation, and the order of participation as illustrated in FIG. 9 by way of example and not limitation. Other party combinations, timings, and/or orders of participating in a session have been contemplated by the present inventors and are within the scope of the present document. For example, an information exchange session may include any combination of and order of patient and human assistant(s), patient and SVA, patient and SVA and human assistant(s).

Figure 10:
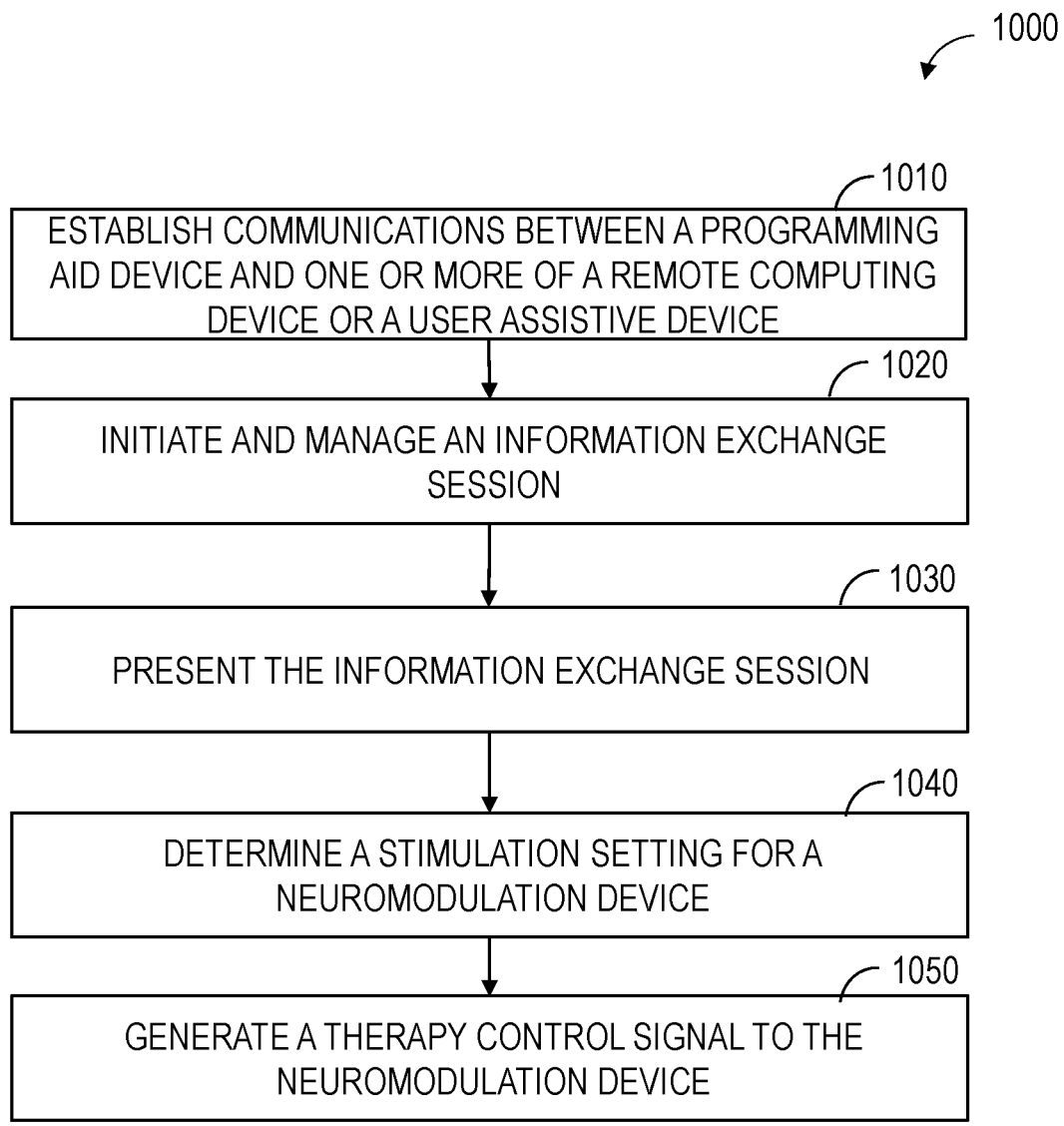
FIG. 10 illustrates, by way of example and not limitation, a method for programming a neuromodulation device using a programming aid device to manage and relieve pain in a patient.

FIG. 10 illustrates, by way of example and not limitation, a method 1000 for programming a neuromodulation device using a programming aid device, such as the PAD 140 or the PAD 310 as described above, to manage and relieve pain in a patient. The method 1000 may be implemented in a medical system, such as the computer-assisted pain mapping and neuromodulation system 300.

The method 1000 begins at step 1010, where communications between a programming aid device operable by a patient, and one or more of a remote computing device, or a user assistive device. The communications can be over a communication network, such as Internet. In an example, the programming aid device can take the form of a personal mobile electronic device, such as a smart phone, a smart watch, a smart wristband, a laptop computer, a tablet, among other mobile electronic devices holdable or wearable by the patient. The programming aid device may be connected to Internet via a cellular network, a WiFi network, or a physical connection such as Ethernet or modem. The user assistive device, such as the user assistive device 150, may be operated by one or more human assistants including, for example, medical professionals, caregivers, or device experts such as device manufacturer representatives. The remote computing device, such as the remote computing device 160, may be a cloud-computing device or networked devices hosting services including a software-based virtual agent (SVA). The SVA may use one or more of scripted rules, artificial intelligence (AI) applications, machine learning (ML) algorithms, or natural language processing and understanding applications, to interpret and discern patient descriptions and requests, and provide services including pain or paresthesia assessment, localization (i.e., identifying pain or paresthesia sites), characterization, diagnostics, and recommending a neuromodulation therapy for pain management and relief.

At 1020, an information exchange session may be initiated such as on the programming aid device. The information exchange session may include messages exchanged between the patient and one or more of the SVA or the human assistant regarding pain or paresthesia perception and pain management of the patient. In an example, the information exchange session may be run on a remotely-accessible pain management platform, such as a software application ("app") installed and run on the programming aid device.

The information exchange session may include conversational messages between the patient and the SVA and/or one or more human assistants. Parties participating in the information exchange session, their respective timings of participation, or the order of participation may be controlled by the controller circuit of the programming aid device, as discussed in the examples with reference to FIG. 9.

In an example, the information exchange session may include information about mapping pain or paresthesia perception onto a body surface map, as described above in the examples with reference to FIG. 6. The SVA may interpret and discern patient description about his or her pain or paresthesia perception, and guide the patient to identify pain or paresthesia sites, such as one or more grid cells of a gridded body surface map, as shown in FIG. 6. In addition to pain or paresthesia sites, in some examples, the SVA may assist the patient to add one or more pain or paresthesia characteristics, such as intensity, quality, type of pain or paresthesia, to the body surface map.

In another example, the information exchange session may include messages about configuring a neuromodulation device to deliver a pain therapy, such as determining or adjusting a stimulation setting for the neuromodulation device, as described in the examples with reference to FIGS. 7-8. For example, the patient may identify one or more stimulation areas where electrostimulation treatment is desirable, or to be withheld or otherwise adjusted. The SVA may guide the patient to label or mark the identified stimulation areas on the body surface map. A new stimulation setting may be generated based on the identified stimulation area. The patient may choose to apply the new stimulation setting, or revert to the previous setting.

In some examples, a human assistant may join an information exchange session per request by the patient or the SVA. An alert may be generated by the programming aid device and sent to the user assistive device to invite the human assistant to join the information exchange session. Additionally or alternatively, such an alert to invite the human assistant may be generated in response to a trigger event, such as an identification of a new pain or paresthesia site identified by the patient, a new stimulation setting different from the existing stimulation setting and suggested by the SVA or requested by the patient, a frequent reprogramming of therapy exceeding a threshold, the SA recommending a tighter parameter guard rails, or an outlier event during programming of therapy, among others. The human assistant may confirm, override, or modify a stimulation setting suggested by the SVA.

In some examples, the information exchange session may include messages about integrity testing or trouble-shooting of the neuromodulation device, such as checking battery status, connections among components of the neuromodulation device. In some examples, information exchange sessions may be tracked over time, and stored in a storage device.

At 1030, information exchanges during the session may be presented on a user interface of the programming aid device. The exchanged information may be presented in one or more of textual, graphical, audio, or video forms. FIGS. 6-8 as described above illustrate some non-limiting examples of information exchange session as displayed on a user interface of the programming aid device, such as a smart phone.

At 1040, a stimulation setting for the neuromodulation device may be determined based on the information exchange. The stimulation setting may include an electrode configurations, stimulation pulse amplitude, pulse width, rate (or frequency), waveform of the electrical pulses, fractionalized current distribution to the electrodes (as percentage cathodic current, percentage anodic current, or off), among others. At 1050, a therapy control signal can be generated and applied to the neuromodulation device to initiate delivery of neuromodulation energy to the patient in accordance with the determined stimulation setting.

Figure 11:
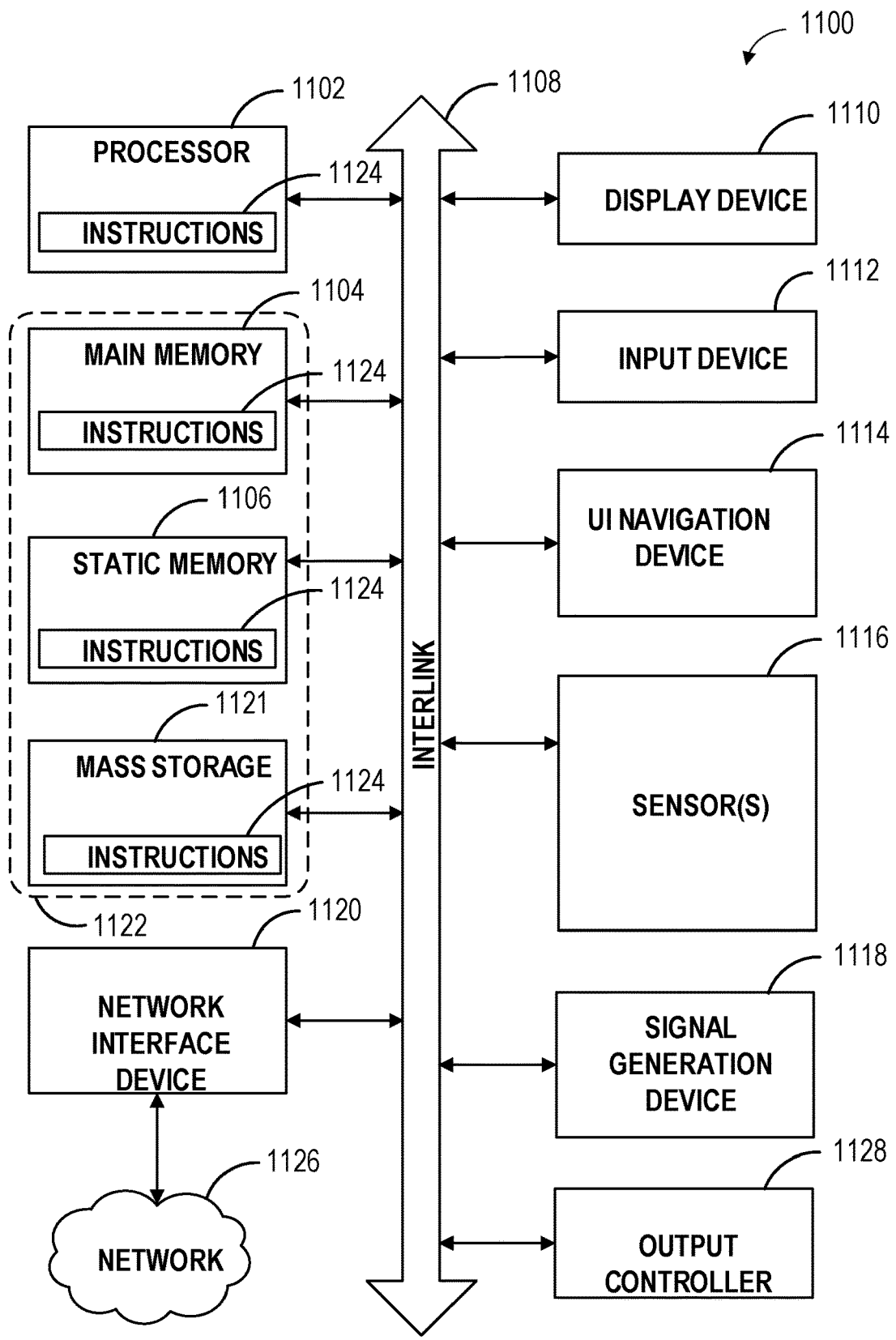
FIG. 11 illustrates generally a block diagram of an example machine 1100 upon which any one or more of the techniques (e.g., methodologies) discussed herein may perform.

FIG. 11 illustrates generally a block diagram of an example machine 1100 upon which any one or more of the techniques (e.g., methodologies) discussed herein may perform. Portions of this description may apply to the computing framework of various portions of the computer-assisted pain mapping and neuromodulation system 300, such as the PAD 310.

In alternative embodiments, the machine 1100 may operate as a standalone device or may be connected (e.g., networked) to other machines. In a networked deployment, the machine 1100 may operate in the capacity of a server machine, a client machine, or both in server-client network environments. In an example, the machine 1100 may act as a peer machine in peer-to-peer (P2P) (or other distributed) network environment. The machine 1100 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1100 may include a hardware processor 1102 (e.g., a central processing unit (CPU), a graphics processing unit (GPU), a hardware processor core, or any combination thereof), a main memory 1104 and a static memory 1106, some or all of which may communicate with each other via an interlink (e.g., bus) 1108. The machine 1100 may further include a display unit 1110 (e.g., a raster display, vector display, holographic display, etc.), an alphanumeric input device 1112 (e.g., a keyboard), and a user interface (UI) navigation device 1114

(e.g., a mouse). In an example, the display unit 1110, input device 1112 and UI navigation device 1114 may be a touch screen display. The machine 1100 may additionally include a storage device (e.g., drive unit) 1116, a signal generation device 1118 (e.g., a speaker), a network interface device 1120, and one or more sensors 1121, such as a global positioning system (GPS) sensor, compass, accelerometer, or other sensor. The machine 1100 may include an output controller 1128, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1116 may include a machine readable medium 1122 on which is stored one or more sets of data structures or instructions 1124 (e.g., software) embodying or utilized by any one or more of the techniques or functions described herein. The instructions 1124 may also reside, completely or at least partially, within the main memory 1104, within static memory 1106, or within the hardware processor 1102 during execution thereof by the machine 1100. In an example, one or any combination of the hardware processor 1102, the main memory 1104, the static memory 1106, or the storage device 1116 may constitute machine readable media.

While the machine readable medium 1122 is illustrated as a single medium, the term "machine readable medium" may include a single medium or multiple media (e.g., a centralized or distributed database, and/or associated caches and servers) configured to store the one or more instructions 1124.

The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1124 may further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1120 may include one or more physical jacks (e.g., Ethernet, coaxial, or phone jacks) or one or more antennas to connect to the communications network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for computer-assisted programming of a neuromodulation device for pain management in a patient, the system comprising:
   a programming aid device operable by the patient, comprising:
   a user interface;
   a transceiver circuit configured to receive, from one or more of a software-based virtual agent (SVA) or a human assistant other than the patient, information about pain management for the patient; and
   a controller circuit configured to:
   initiate and manage an information exchange session between the patient and the SVA, via the user interface, regarding pain or paresthesia perception and pain management of the patient;
   in response to a trigger event detected by the programming aid device, generate an alert to invite the human assistant to join the information exchange session while it is going on;
   based on the information exchange among the patient, the SVA, and the human assistant, determine a stimulation setting for the neuromodulation device; and
   generate a therapy control signal to the neuromodulation device to initiate delivery of neuromodulation energy to the patient in accordance with the determined stimulation setting.

2. The system of claim 1, wherein the programming aid device is a personal mobile electronic device.

3. The system of claim 1, wherein the transceiver circuit is configured to communicate with at least one of a remote computing device hosting services including the SVA, or a user assistive device operable by the human assistant to provide the information about pain management.

4. The system of claim 1, wherein the user interface is configured to receive and present the exchanged information in one or more of textual, graphical, audio, or video forms.

5. The system of claim 1, wherein the information exchange session includes messages about pain or paresthesia perception of the patient including identifying one or more pain or paresthesia sites, and
 wherein the controller circuit is configured to generate a pain or paresthesia map based on the identified one or more pain or paresthesia sites.

6. The system of claim 5, wherein the messages about pain or paresthesia perception includes determining one or more pain or paresthesia characteristics including an intensity, a type, or a quality of pain or paresthesia at respective one or more pain or paresthesia sites, and
 wherein the controller circuit is configured to generate a pain or paresthesia map further using at least one of the one or more pain or paresthesia characteristics.

7. The system of claim 1, wherein the information exchange session includes messages about identifying one or more stimulation sites to apply the neuromodulation energy or modified neuromodulation energy, and
 wherein the controller circuit is configured to determine the stimulation setting based on the identified one or more stimulation sites.

8. The system of claim 1, wherein the information exchange session includes the SVA or the human assistant suggesting a stimulation setting for the neuromodulation device, and
 wherein the controller circuit is configured to determine the stimulation setting based on suggested stimulation setting.

9. The system of claim 1, wherein the information exchange session includes the human assistant confirming, overriding, or modifying a stimulation setting for the neuromodulation device suggested by the SVA or the patient, and
 wherein the controller circuit is configured to determine the stimulation setting based on the confirmation, override, or modification of the stimulation setting.

10. The system of claim 1, wherein the controller circuit is configured to generate the alert to invite the human assistant to join the information exchange session further responsive to a request by the patient or the SVA.

11. The system of claim 1, wherein the trigger event to cause the alert to invite the human assistant to join the information exchange session includes at least one of:
 an identification of a new pain or paresthesia site;
 a new stimulation setting suggested by the SVA;
 a frequent reprogramming of therapy exceeding a threshold; or
 an outlier event during programming of therapy.

12. The system of claim 1, wherein the controller circuit is configured to generate a control signal that permits or prohibits respective actions of one or more of the patient, the SVA, or the human assistant during the information exchange session.

13. A non-transitory machine-readable storage medium that includes instructions that, when executed by one or more processors of a machine, cause the machine to perform operations comprising:
 establishing communications between a programming aid device operable by a patient and one or more of (1) a remote computing device hosting a software-based virtual agent (SVA) or (2) a user assistive device operable by a human assistant other than the patient;
 initiating and managing an information exchange session, via the programming aid device, between the patient and the SVA regarding pain or paresthesia perception and pain management of the patient;
 in response to a trigger event detected by the programming aid device, generating an alert to invite the human assistant to join the information exchange session while it is going on;
 presenting the information exchange session on a user interface of the programming aid device;
 based on the information exchange among the patient, the SVA, and the human assistant, determining a stimulation setting for a neuromodulation device; and
 generating a therapy control signal to the neuromodulation device to initiate delivery of neuromodulation energy to the patient in accordance with the determined stimulation setting.

14. The non-transitory machine-readable storage medium of claim 13, wherein the information exchange session includes messages presented in one or more of textual, graphical, audio, or video forms.

15. The non-transitory machine-readable storage medium of claim 13, wherein the information exchange session includes messages about pain or paresthesia perception of the patient including identifying one or more pain or paresthesia sites, and
 wherein the instructions cause the machine to perform operations comprising generating a pain or paresthesia map based on the messages of pain or paresthesia perception.

16. The non-transitory machine-readable storage medium of claim 13, wherein the information exchange session includes messages about identifying one or more stimulation sites to apply the neuromodulation energy or modified neuromodulation energy, and
 wherein the instructions cause the machine to perform operations comprising determining the stimulation setting based on the identified one or more stimulation sites.

17. The non-transitory machine-readable storage medium of claim 13, wherein the instructions cause the machine to perform operations comprising generating the alert to invite the human assistant to join the information exchange session further responsive to a request by the patient or the SVA.

18. A method of programming of a neuromodulation device for pain management in a patient using a programming aid device, comprising:
 establishing communications between the programming aid device and one or more of (1) a remote computing device hosting a software-based virtual agent (SVA) or (2) a user assistive device operable by a human assistant other than the patient;
 initiating and managing an information exchange session, via the programming aid device, between the patient and the SVA regarding pain or paresthesia perception and pain management of the patient;
 in response to a trigger event detected by the programming aid device, generating an alert to invite the human assistant to join the information exchange session while it is going on;
 presenting the information exchange session on a user interface of the programming aid device;
 based on the information exchange among the patient, the SVA, and the human assistant, determining a stimulation setting for the neuromodulation device; and generating a therapy control signal to the neuromodulation device to initiate delivery of neuromodulation energy to the patient in accordance with the determined stimulation setting.

19. The method of claim 18, wherein the information exchange session includes messages about pain or paresthesia perception of the patient including identifying one or more pain or paresthesia sites, and the method comprises generating a pain or paresthesia map based on the messages of pain or paresthesia perception.

20. The method of claim 18, wherein the information exchange session includes messages about identifying one or more stimulation sites to apply the neuromodulation energy or modified neuromodulation energy, and the method comprises determining the stimulation setting based on the identified one or more stimulation sites.

* * * * *